United States Patent
Zhao et al.

(10) Patent No.: US 9,867,669 B2
(45) Date of Patent: Jan. 16, 2018

(54) CONFIGURATION MARKER DESIGN AND DETECTION FOR INSTRUMENT TRACKING

(75) Inventors: Tao Zhao, Sunnyvale, CA (US); Wenyi Zhao, Sunnyvale, CA (US); William C. Nowlin, Los Altos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 872 days.

(21) Appl. No.: 12/428,691

(22) Filed: Apr. 23, 2009

(65) Prior Publication Data

US 2010/0168763 A1    Jul. 1, 2010

Related U.S. Application Data

(60) Provisional application No. 61/203,975, filed on Dec. 31, 2008.

(51) Int. Cl.
*G06K 9/00* (2006.01)
*A61B 34/20* (2016.01)
(Continued)

(52) U.S. Cl.
CPC .............. *A61B 34/20* (2016.02); *A61B 34/30* (2016.02); *A61B 34/37* (2016.02); *A61B 90/94* (2016.02);
(Continued)

(58) Field of Classification Search
CPC .... A61B 2019/5437; A61B 2019/5255; A61B 19/5244
(Continued)

(56) References Cited

U.S. PATENT DOCUMENTS 4,614,366 A   9/1986 North et al.
5,572,999 A * 11/1996 Funda ................. A61B 1/00193
                                                      600/118
(Continued)

FOREIGN PATENT DOCUMENTS

WO   WO-2005102202 A1   11/2005
WO   WO-2006091494 A1    8/2006
(Continued)

OTHER PUBLICATIONS

Fergus (A Sparse Category Model for Efficient Learning and Exhaustive Recogniztion) CVPR 2005 Proceedings of the 2005 IEEE Computer Society Conference on Computer Vision and Pattern Recognition, vol. 1.*
(Continued)

*Primary Examiner* — Ellsworth Weatherby

(57) ABSTRACT

The present disclosure relates to systems, methods, and tools for tool tracking using image-derived data from one or more tool located reference features. A method includes: directing illuminating light from a light source onto a robotic surgical tool within a patient body, wherein the tool includes a plurality of primitive features having known positions on the tool, and wherein each feature includes a spherical reflective surface; capturing stereo images of the plurality of primitive features when the tool is within the patient body, wherein the stereo images are captured by an image capture device adjacent the illumination source so that the illumination light reflected from the imaged primitive features toward the image capture device substantially aligns with spherical centers of the surfaces of the imaged primitive features, and determining a position for the tool by processing the stereo images so as to locate the spherical centers of the imaged primitive features by using the reflected light.

16 Claims, 27 Drawing Sheets

(51) Int. Cl.
*A61B 34/30* (2016.01)
*A61B 34/37* (2016.01)
*A61B 90/94* (2016.01)
A61B 90/00 (2016.01)
A61B 34/10 (2016.01)

(52) U.S. Cl.
CPC . *A61B 2034/102* (2016.02); *A61B 2034/2065* (2016.02); *A61B 2090/371* (2016.02); *A61B 2090/3983* (2016.02)

(58) Field of Classification Search
USPC ............... 318/568.21; 378/205; 382/159; 600/117, 407, 424, 426, 429
See application file for complete search history.

(56) References Cited

U.S. PATENT DOCUMENTS

| | | | |
|---|---|---|---|
| 5,836,869 A | 11/1998 | Kudo et al. | |
| 5,848,967 A | 12/1998 | Cosman | |
| 5,891,034 A | 4/1999 | Bucholz | |
| 6,006,126 A | 12/1999 | Cosman | |
| 6,122,541 A | 9/2000 | Cosman et al. | |
| 6,167,295 A | 12/2000 | Cosman | |
| 6,201,984 B1 | 3/2001 | Funda et al. | |
| 6,246,900 B1 | 6/2001 | Cosman et al. | |
| 6,275,725 B1 | 8/2001 | Cosman | |
| 6,351,661 B1 | 2/2002 | Cosman | |
| 6,405,072 B1 | 6/2002 | Cosman | |
| 6,434,416 B1 | 8/2002 | Mizoguchi et al. | |
| 6,468,265 B1 * | 10/2002 | Evans et al. | 606/1 |
| 6,826,423 B1 | 11/2004 | Hardy et al. | |
| 7,072,704 B2 | 7/2006 | Bucholz | |
| 7,137,712 B2 * | 11/2006 | Brunner | G01B 11/24 359/534 |
| 7,747,311 B2 | 6/2010 | Quaid et al. | |
| 7,797,032 B2 | 9/2010 | Martinelli et al. | |
| 7,831,292 B2 | 11/2010 | Quaid et al. | |
| 2002/0065461 A1 | 5/2002 | Cosman | |
| 2002/0188194 A1 | 12/2002 | Cosman | |
| 2002/0193686 A1 | 12/2002 | Gilboa | |
| 2003/0210812 A1 | 11/2003 | Khamene et al. | |
| 2004/0002642 A1 * | 1/2004 | Dekel et al. | 600/407 |
| 2004/0052333 A1 | 3/2004 | Sayre et al. | |
| 2004/0138556 A1 * | 7/2004 | Cosman | 600/424 |
| 2005/0182295 A1 | 8/2005 | Soper et al. | |
| 2006/0142657 A1 * | 6/2006 | Quaid et al. | 600/424 |
| 2006/0241400 A1 | 10/2006 | Bucholz | |
| 2006/0258938 A1 * | 11/2006 | Hoffman | A61B 1/00193 600/424 |
| 2007/0013336 A1 | 1/2007 | Nowlin et al. | |
| 2007/0167702 A1 | 7/2007 | Hasser et al. | |
| 2007/0183041 A1 * | 8/2007 | McCloy | G01S 5/16 359/515 |
| 2007/0265527 A1 | 11/2007 | Wohlgemuth | |
| 2008/0132909 A1 | 6/2008 | Jascob et al. | |
| 2008/0240551 A1 | 10/2008 | Zitnick et al. | |
| 2008/0262345 A1 * | 10/2008 | Fichtinger | A61B 6/504 600/426 |
| 2008/0285724 A1 | 11/2008 | Dehler | |
| 2010/0168562 A1 | 7/2010 | Zhao et al. | |

FOREIGN PATENT DOCUMENTS

| | | |
|---|---|---|
| WO | WO-2006124388 A1 | 11/2006 |
| WO | WO-2006131373 A2 | 12/2006 |
| WO | WO-2007090288 A1 | 8/2007 |

OTHER PUBLICATIONS

Hynes et al., Uncalibrated Visual-Servoining of a Dual-Arm Robot for MIS Suturing, Biomedical Robotics and Biomechatronics, 2006, 420-426.*

Comport, Andrew Ian. "Towards a Computer Imagination: Robust Real-time 3D Tracking of Rigid and Articulated Objects for Augmented Reality and Robotics."). University of Rennes 1 (2005). ftp://ftp.irisa.fr/techreports/theses/2005/comport.pdf.*

Fergus et al., Weakly Supervised Scale-Invariant Learning of Models for Visual Recognition, International Journal of Computer Vision 71(3), 273-303, 2007.*

PCT/US09/68423 International Search Report and Written Opinion of the International Searching Authority, mailed Mar. 3, 2010, 15 pages.

Kosaka, Akio et al., "Augmented Reality System for Surgical Navigation Using Robust Target Vision," IEEE Conference on Computer Vision and Pattern Recognition, 2000, vol. 2, pp. 187-194.

PCT/US09/68395 International Search Report and Written Opinion of the International Searching Authority, mailed Mar. 29, 2010, 14 pages.

Burschka, Darius et al., "Navigating Inner Space: 3-D Assistance for Minimally Invasive Surgery," Robotics and Autonomous Systems, 2005, pp. 5-26; vol. 52—Issue 1, Elsevier.

Casals, A. et al., "Automatic Guidance of an Assistant Robot in Laparoscopic Surgery," 1996 IEEE International Conference on Robotics and Automation (ICRA '96), Minneapolis, MN, Apr. 1996, pp. 895-900.

Climent, Joan and Pere Mares, "Automatic Instrument Localization in Laparoscopic Surgery," Electronic Letters on Computer Vision and Image Analysis, vol. 4, Issue 1, pp. 21-31, 2004.

Doignon, C. et al., "Real-time Segmentation of Surgical Instruments Inside the Abdominal Cavity Using a Joint Hue Saturation Color Feature," Real-Time Imaging, vol. 11, pp. 429-442, 2005.

Doignon, Christophe et al., "The Role of Insertion Points in the Detection and Positioning of Instruments in Laparoscopy for Robotic Tasks," Proceedings of Medical Image Computing and Computer-Assisted Intervention Conference (MICCAI) 2006, Lecture Notes in Computer Science 4190, Springer, pp. 527-534, 2006.

Dutkiewicz, Piotr et al., "Visual Tracking of Surgical Tools for Laparoscopic Surgery," Fourth International Workshop on Robot Motion and Control (RoMoCo '04), Jun. 17-20, 2004, pp. 23-38.

Kato, Hirokazu and Mark Billinghurst, "Marker Tracking and HMD Calibration for a Video-based Augmented Reality Conferencing System," 2nd IEEE and ACM Workshop on Augmented Reality, Oct. 20-21, 1999, pp. 85-94.

Kim, Min-Seok et al., "Real-Time Visual Tracking for Laparoscopic Surgery," International Journal of Human-Friendly Welfare Robotic Systems, vol. 5, Issue 1, pp. 2-9, 2004.

Krupa, Alexandre et al., "Autonomous 3-D Positioning of Surgical Instruments in Robotized Laparoscopic Surgery Using Visual Servoing," IEEE Transactions on Robotics and Automation, vol. 19, No. 5, pp. 842-853, Oct. 2003.

Lopez De Ipiña, Diego et al., "TRIP: A Low-Cost Vision-based Location System for Ubiquitous Computing," Personal and Ubiquitous Computing, vol. 6, pp. 206-219, 2002.

McKenna, S.J. et al., "Towards Video Understanding of Laparoscopic Surgery: Instrument Tracking," Image and Vision Computing New Zealand (IVCNZ '05), Dunedin, Nov. 28-29, 2005, 5 pages.

Mooser, Jonathan et al., "Triocodes: A Barcode-like Fiducial Design for Augmented Reality Media," IEEE International Conference on Multimedia and Expo (ICME), Jul. 2006, pp. 1301-1304.

Naimark, Leonid and Eric Foxlin, "Circular Data Matrix Fiducial System and Robust Image Processing for a Wearable Vision-Inertial Self-Tracker," International Symposium on Mixed and Augmented Reality (ISMAR '02), Sep. 30-Oct. 1, 2002, pp. 27-36.

Rekimoto, Jun and Yuji Ayatsuka, "CyberCode: Designing Augmented Reality Environments with Visual Tags," Proceedings of DARE 2000 on Designing Augmented Reality Environments, Elsinore, Denmark, Internet: http://ftp.csl.sony.co.jp/person/rekimoto/papers/dare2000.pdf.

Setrix, Inc., "Novel Applications and Sunshiny Markers," White paper, 9 pages, 2003, Internet: http://www.setrix.net/pdf/papers/SetrixLogistics.pdf.

(56) References Cited

OTHER PUBLICATIONS

Uecker, Darrin R. et al., "Automated Instrument Tracking in Robotically-Assisted Laparoscopic Surgery," Journal of Image Guided Surgery, vol. 1, No. 6, pp. 308-325, 1998.
Vertut, Jean et al., Robot Technology: Teleoperation and Robotics Evolution and Development, 1986, vol. 3A, 332 pages, English translation Prentice-Hall, Inc., Inglewood Cliffs, NJ, USA.
Voros, Sandrine et al., "Automatic Detection of Instruments in Laparoscopic Images: A First Step Towards High Level Command of Robotized Endoscopic Holders," International Journal of Robotics Research, vol. 26, Issue 11-12, pp. 1173-1190, Nov.-Dec. 2007.
Wei, Guo-Quing et al., "Real-Time Visual Servoing for Laparoscopic Surgery," IEEE Engineering in Medicine and Biology Magazine, Jan./Feb. 1997, pp. 40-45, vol. 16—Issue 1, IEEE.
Zhang, Xiaoli and Shahram Payandeh, "Application of Visual Tracking for Robotic-Assisted Laparoscopic Surgery," Journal of Robotic Systems, vol. 19, No. 7, pp. 315-328, 2002.
Final Office Action mailed Nov. 23, 2011 for U.S. Appl. No. 12/428,657, filed Apr. 23, 2009.
Non-Final Office Action mailed Jun. 9, 2011 for U.S. Appl. No. 12/428,657, filed Apr. 23, 2009.
Non-Final Office Action mailed Sep. 13, 2012 for U.S. Appl. No. 12/428,657, filed Apr. 23, 2009.
Final Office Action mailed Mar. 21, 2013 for U.S. Appl. No. 12/428,657, filed Apr. 23, 2009.
Office Action mailed Feb. 13, 2015 for European Application No. 20090775495 filed Dec. 17, 2009, 5 pages.
Office Action mailed Jun. 18, 2013 for Chinese Application No. 20098157767 filed Dec. 17, 2009, 24 pages.
Office Action mailed Jan. 21, 2014 for Chinese Application No. 20098157767 filed Dec. 17, 2009, 25 pages.
Office Action mailed Jul. 22, 2014 for Chinese Application No. 20098157767 filed Dec. 17, 2009, 21 pages.
Office Action mailed Nov. 6, 2015 for European Application No. 09775495.6 filed Dec. 17, 2009, 4 pages.
Office Action mailed Aug. 9, 2016 for Korean Application No. 10-2011-7017601 filed Jul. 27, 2011, 10 pages.
Office Action mailed Feb. 11, 2016 for Korean Application No. 10-2011-7017601 filed Jul. 27, 2011, 10 pages.

* cited by examiner

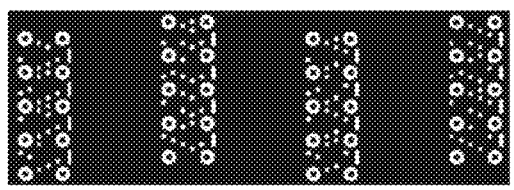
FIG. 17A
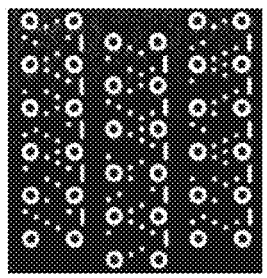
FIG. 16A
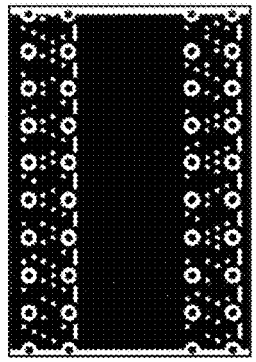
FIG. 15A
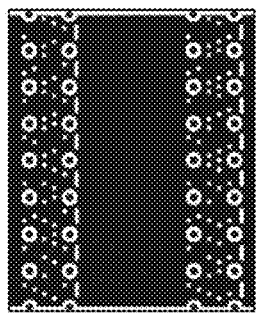
FIG. 14A
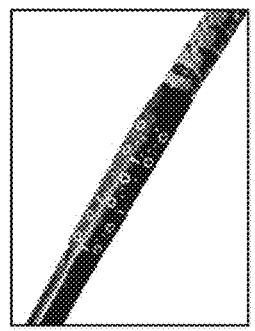
FIG. 17B
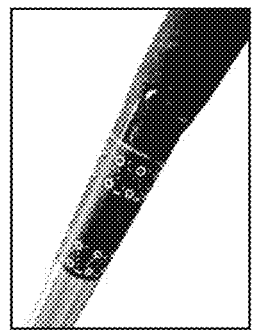
FIG. 16B
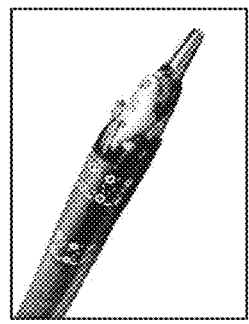
FIG. 15B
FIG. 14B

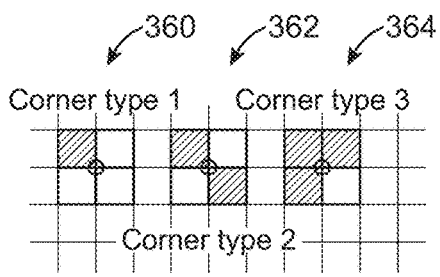
FIG. 29A     FIG. 29B     FIG. 29C
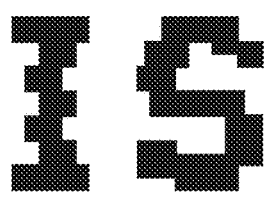 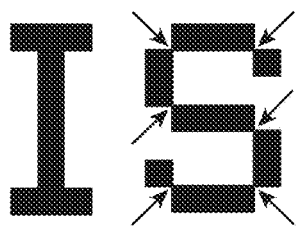 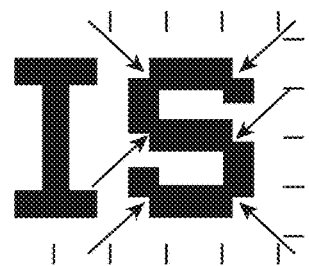
FIG. 29D     FIG. 29E     FIG. 29F
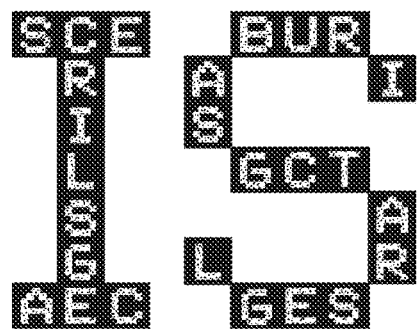 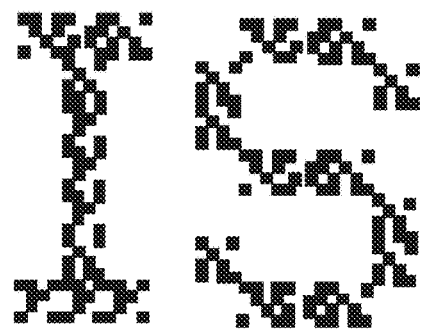
FIG. 29G     FIG. 29H

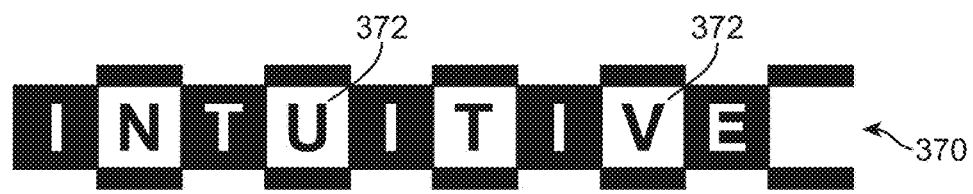
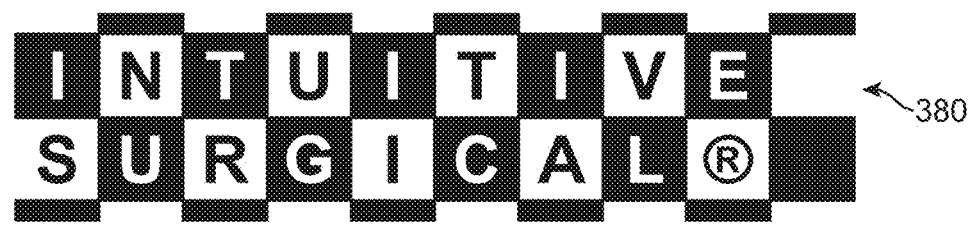
FIG. 30A
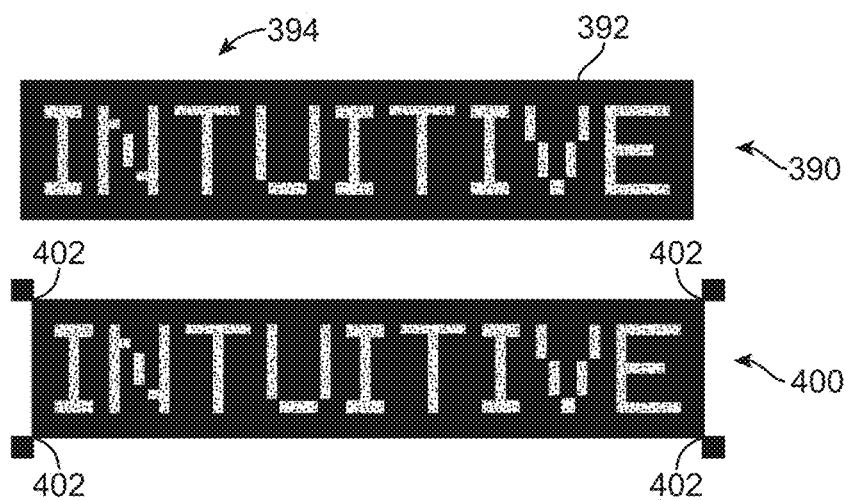
FIG. 30B
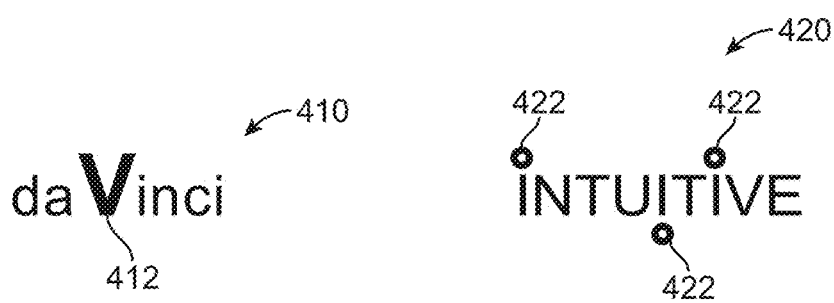
FIG. 30C　　　　　　　FIG. 30D

CONFIGURATION MARKER DESIGN AND DETECTION FOR INSTRUMENT TRACKING

RELATED APPLICATION

This non-provisional application claims the benefit under 35 U.S.C. §119(e) of provisional U.S. Pat. App. No. 61/203,975 (filed Dec. 31, 2008), which is incorporated herein by reference.

This application is related to non-provisional U.S. patent application Ser. No. 12/428,657 (concurrently filed) [entitled "Fiducial Marker Design and Detection for Locating Surgical Instrument in Images"] and to provisional U.S. Pat. App. No. 61/204,084 (filed Dec. 31, 2008), both of which are incorporated herein by reference.

BACKGROUND

Minimally-invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally-invasive surgical techniques. Also, patient recovery times, patient discomfort, surgical side effects, and time away from work may, also be reduced with minimally-invasive surgery.

A common form of minimally-invasive surgery is endoscopy, and a common form of endoscopy is laparoscopy, which is minimally-invasive inspection and surgery inside the abdominal cavity. In standard laparoscopic surgery, a patient's abdomen is insulated with gas, and cannula sleeves are passed through small (approximately ½ inch or less) incisions to provide entry ports for laparoscopic instruments.

Laparoscopic surgical instruments generally include a laparoscope or an endoscope (for viewing the surgical field), and working tools. The working tools are similar to those used in conventional (open) surgery, except that the working end or end effector of each tool is separated from its handle by an extension tube. As used herein, the term "end effector" means the actual working part of the surgical instrument and can include clamps, graspers, scissors, staplers, and needle holders, for example.

To perform surgical procedures, the surgeon passes these working tools or instruments through cannula sleeves to an internal surgical site and manipulates them from outside the abdomen. The surgeon views the procedure by means of a monitor that displays an image of the surgical site taken from the laparoscope. Similar endoscopic techniques are employed in, e.g., arthroscopy, retroperitoneoscopy, pelviscopy, nephroscopy, cystoscopy, cisternoscopy, sinoscopy, hysteroscopy, urethroscopy, and the like.

Minimally-invasive telesurgical robotic systems are being developed to increase a surgeon's dexterity, when working within an internal surgical site, as well as to allow a surgeon to operate on a patient from a remote location. In a telesurgery system, the surgeon is often provided with an image of the surgical site at a control console. While viewing a three-dimensional (3-D) image of the surgical site on a suitable viewer or display, the surgeon performs the surgical procedures on the patient by manipulating master input or control devices of the control console. Each of the master input devices controls the motion of a servomechanically operated surgical instrument. During the surgical procedure, the telesurgical system can provide mechanical actuation and control of a variety of surgical instruments or tools having end effectors that perform various functions for the surgeon, e.g., holding or driving a needle, grasping a blood vessel, dissecting tissue, or the like, in response to manipulation of the master input devices.

During the surgical procedure, however, the surgeon may manipulate the tool so that its end effector is moved outside of the endoscope's field of view, or the end effector may become difficult to see due to occlusion by fluids or other intervening objects. In such cases it would be useful to be able to provide assistance to the surgeon in locating and/or identifying the end effector on the work-station's display screen. Accurate information regarding a tool's 3-D pose (location and orientation) can be used to provide this assistance. In general, accurate information of a tool's 3-D pose is important for a number of image guided surgical and user interface applications.

One approach that has been used to provide accurate tool tracking involves a fusion of kinematics-based pose information with image-derived pose information. Such a fusion of tool tracking information can provide the advantages of both types of data without the associated disadvantages. While kinematics joint data are usually available at a very high update rate, a kinematics estimated pose may not be very accurate due to error accumulation at each joint, with errors in joints located farther away from the tool having a greater impact on accuracy. In contrast, image-derived tool pose estimation can be highly accurate, but may run at a slower update rate that what is useful for many real-time applications. By correcting the higher-update kinematics-pose estimation using the more accurate image-derived tool pose estimation, a more accurate higher-update tool pose estimation can be obtained.

Some existing technologies have been used for surgical tool tracking. In one approach, an optical tracker is used to track the position of a marker assembly that is attached to a location on the surgical instrument outside the patient's body. However, the optical tracker requires a dedicated stereo camera and dedicated lighting, which take space in an already crowded operating room. Attaching such optical trackers also reduces the range of motion of the robotic arms due to the potential for collision. There can also be some level of error that results from propagating the 3-D pose to the surgical tool tip. Additional problems include: the extra space required, limited visibility range, the added hardware setup in the operating room, and cost. Another approach uses an electromagnetic tracker, which has its own associated disadvantages. For example, most surgical instruments have metal parts that can cause distortion, which can vary in time due to changes in distances between an electromagnetic tracker attached to one tool tip and metal components of an adjacent surgical tool. An electromagnetic tracker also involves extra cost.

Computing the 3-D pose of a rigid body with respect to a camera is a well-studied problem in computer/robot vision. A 3-D pose can be solved by starting with the known features of an object and matching these features with their 2D correspondence in the image. Features such as point and line segments are commonly used. Determination of the 3-D pose of a rigid body from a single 2D image is referred to as "pose estimation" in computer vision (see introduction in Christophe Doignon, "Scene Reconstruction, Pose Estimation and Tracking," 2007). If using point-based correspondences, the problem is known as "perspective-n-point," where n is the number of correspondences. Three non-collinear points provides four solutions. Four or more non-collinear points provides a unique solution.

Determination of the 3-D pose of a rigid object using a stereo camera can be accomplished using two approaches. First, the determination of the 3-D pose can be approached as an optimization problem where the 3-D pose is selected that provides the best fit between the projected 3-D points With the image correspondences in both images. In the other approach, image points in both views can be used to determine corresponding 3-D points using stereo triangulation and relative pose is determined by solving a rigid transformation between the determined 3-D points and corresponding model points. (See A. Lorusso. D. W. Eggert and R. B. Fisher, "A comparison of four algorithms for estimating 3-d rigid transformations," 1995.)

However, a number of factors can hamper the ability to obtain an image-derived tool pose estimation. For one, an image-derived estimate is only available when the object's features are within the field of view of the imaging device(s) and they can be extracted. Some of the factors that may prevent the extraction of features include: occlusion of the features by anatomical structure or other instruments, degenerated image quality caused by fast instrument or camera motion (i.e., motion blur), adverse lighting conditions (e.g., saturation when the light is too strong, lack of contrast when the light is too weak, strong specularity due to the relative geometric configurations of the light source, instrument, and imaging device), and complex background clutter.

More reliable image-derived tool pose estimation would, therefore, be beneficial in order to increase the rate at which highly-accurate tool pose estimates are available, which in turn may help to provide more accurate overall tool tracking. Accordingly, improved methods and systems providing improved image-derived tool pose estimates would be desirable, particularly those with reduced sensitivities to adverse conditions, such as occlusions, motion blur, and adverse lighting conditions.

BRIEF SUMMARY

In accordance with embodiments, improved systems, methods, and tools for performing 3-D tool tracking using image-derived data from one or more tool located reference features are provided. The use of one or more reference features can provide for improved image-derived tool pose estimation by supplying one or more features that can be more reliably imaged and processed. Effective and reliable image-derived tool pose estimation can be particularly useful during minimally-invasive surgery, where accurate and reliable tool tracking can provide a number of advantages, such as to provide assistance to a Surgeon in locating an occluded or out-of-view tool. However, it is appreciated that the disclosed systems, methods, and tools can be used in a wide variety of applications, both inside and outside a human body, as well as in non-surgical tool tracking applications. In general, accurate information of a tool's 3-D pose is important for a number of image-guided and user interface applications.

Thus, the following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

In accordance with an embodiment, a robotic surgical method for determining a tool state for an imaged tool is provided. The method includes: capturing a first image of a tool that includes multiple features defining a first marker, where at least one of the features of the first marker includes an identification feature: determining a position for the first marker by processing the first image; determining an identification for the first marker by using the at least one identification feature by processing the first image; and determining a tool state for the tool by using the position and the identification of the first marker.

A robotic surgical method for determining a tool state for an imaged tool can involve a number of options. For example, the first marker can include redundant features defining error-checking data and/or check sum data, and the method can include: processing the first image to detect the redundant features and read the error-checking data and/or check sum data; and validating the identification of the first marker by verifying that the first marker identification is consistent with the error-checking data and/or check sum data.

Some options involve a tool having two or more markers. Each of the two or more markers can have at least one identification feature associated with an identification that differs from other markers on the tool. The image processing can be accomplished using a processor having data indicating, for each marker, an associated predetermined positional relationship between the marker and a joint of the surgical tool. Determining a tool state for the tool can include using the position of a first marker, the identification of the first marker, and the associated positional relationship data for the first marker. The first image can include a second marker of the tool. A method can include: determining a position for the second marker by processing the first image; and determining the identification of the second marker by processing the first image; determining a tool state for the tool by using the second marker position, the second marker identification, and the predetermined positional relationship data associated with the second marker.

Some options involve multiple images of a tool. For example, a method can include steps that can be used where the second marker is obscured in the first image, such as: moving the tool after determining the tool state by using the first marker; capturing a second image of the moved tool where the first marker is obscured but the second marker is not obscured; determining a position for the second marker bad processing the second image; determining the identification of the second marker by processing the second image; and determining a moved tool state for the tool using the second marker position, the second marker identification, and the predetermined positional relationship data associated with the second marker.

Some options involve stereo images of a tool. For example, a stereo-imaging device, such as a stereoscopic endoscope, can be used to capture a first and second image of the surgical tool, which can be processed so as to determine 3-D positional data for the first marker. A tool state can be determined in three dimensions or more.

Some options involve tools having multiple markers having certain types of features. For example, each marker can have at least one localizer feature, and at least one identification feature at a known positional relationship relative to at least one localizer feature. The position of the first marker can be determined by using the localizer feature and the orientation feature. The identification of the first marker can be determined by identifying at least one localizer feature of the first marker and reading the identification feature according to the known positional relationship between the localizer feature and the identification feature.

Some options involve a "hypothesis and test" approach. For example, a method can include: processing the first image so as to identify the at least one localizer feature; selecting a candidate identity for the first marker; generating a candidate view of a marker having the candidate identity by using the identified at least one localizer feature; and comparing the candidate view with the first image so as to verify that the selected candidate identity is the first marker identity. Selecting a candidate identity for the first marker can include generating an estimated pose for the surgical tool by using at least one prior tool state from a prior image of the tool or joint data from a robotic actuation system effectuating movement of the tool. The candidate identity can be selected so as to result in a candidate pose for the surgical tool that is within a predetermined deviation of the estimated pose for the surgical tool. A method can include processing an image containing multiple surgical tools, where each surgical tool has an identity. An identity can be associated with an imaged tool having the first marker by verifying that the candidate identity for the first marker results in a candidate pose that is within a predetermined deviation of the estimated pose for the surgical tool having the first marker.

A variety of approaches can be used to determine position data for a marker. For example, a Maximum Stable Extremal Region (MSER) approach can be used. As another example, adaptive thresholding can be used.

In accordance with another embodiment, a robotic surgical system that can be used for determining a tool state for an imaged tool is provided. The system includes: a surgical tool having multiple features defining a first marker, with at least one of the features including an identification feature; an imaging device for capturing a first image of the tool during use and outputting first image data in response thereto; and a processor coupled with the imaging device and adapted to process the first image so as to: determine positional data for the first marker; determine an identification of the first marker by using the identification feature; and determine tool state data for the imaged tool by using the positional data for the first marker and the identification of the first marker.

A robotic surgery system for determining a tool state for an imaged tool can include optional components and/or variations. For example, a system can include a tangible medium that includes machine-readable instructions executable by the processor for processing a captured image. A system can include an input for non-endoscopically derived tool state data that is derived from robotic joints supporting the tool, and the processor can be configured to process the non-endoscopically derived tool state information and the image-derived tool state information for tracking the state of the tool. The imaging device can be adapted to capture a second image of the surgical tool at substantially the same time as the first image and output second image data in response thereto. The processor can be configured so as to determine 3-D positional data for the first marker by processing the first and second image data. The imaging device can include a stereoscopic endoscope.

Optional components and/or variations can involve marker features. For example, a first marker can include redundant features defining error-checking data. The processor can be configured to process the first image data so as to: detect the first marker redundant features; read the error-checking data; and validate the identification of the first marker by verifying that the first marker identification is consistent with the error-checking data Redundant features can also define check sum data and the processor can be configured to process the first image data so as to read the check sum data. The processor can validate the identification of the first marker by verifying that the first marker identification is consistent with the check sum data. Markers can have various configurations. For example, at least one marker can include at least one localizer feature that is shared with an adjacent marker. The features of one or more markers can be arranged in a two-dimensional (2-D) pattern. One or more markers can use circles or corners as localizer features. The corners can include saddle points. One or more markers can include three localizer features. One or more markers can include four localizer features. One or more marker can include four circles and a bar as localizer features. A marker can include text, which can be modified to increase positional data or discriminative features.

Optional components and/or variations can involve multiple markers. Multiple markers can be distributed around a tool and the processor can include data for each marker indicating an associated marker identification and an associated predetermined positional relationship between the marker and a joint of the surgical tool. Multiple markers can have identification features that differ sufficiently for the processor to determine the identification of the markers encompassed within the first image.

A processor can use the determined 3-D pose to modify a displayed image of the tool in a variety of ways. For example, the displayed image can be modified so that the added reference features are less visually obtrusive, or are "erased" entirely by altering portions of the images corresponding to the reference features.

In accordance with another embodiment, a surgical tool for use with a robotic surgery system is provided. The surgery system includes an imaging device for capturing an image of the surgical tool during use and a processor coupled with the imaging device for processing the captured image so as to determine image-derived positional information for the surgical tool. The surgical tool includes multiple markers, where each marker has at least one identification feature. The identification features of each marker differ sufficiently for the surgery system to discriminate between the markers based on images encompassing the markers.

In accordance with another embodiment, a robotic surgical method is provided. The method includes capturing a first image of a surgical tool, the surgical tool including multiple features defining multiple markers where each marker has a predetermined positional relationship with the surgical tool, the first image including one of the markers; determining a position for the imaged marker by processing the first image; generating an estimated tool state for the tool by using at least one prior tool state from a prior image of the tool or joint data from a robotic actuation system effectuating movement of the tool; and determining a tool state for the tool using the position of the imaged marker the predetermined positional relationship between the surgical tool and the imaged marker, and the estimated tool state for the tool.

In accordance with another embodiment, a surgical robotic tool tracking method is provided. The method includes: directing illuminating light from a light source onto a robotic surgical tool within a patient body where the illuminating light includes a visible light spectrum, the tool including a plurality of primitive features having known positions on the tool, and where each feature includes a spherical reflective surface; capturing stereo images of a plurality of the primitive features when the tool is within the patient body the stereo images being captured by a stereo image capture device adjacent the illumination source so that the illumination light reflected from the imaged primitive features towards the image capture device substantially aligns Faith spherical centers of the surfaces of the imaged primitive features; and determining a position for the tool by processing the stereo images so as to locate the spherical centers of the imaged primitive features by using the reflected light.

A surgical robotic tool tracking method can involve a number of options. Determining a position for the tool by processing the image can be accomplished so as to identify at least one of the primitive features by using specular reflected light. The stereo images can be processed so as to determine 3-D positional data for the spherical centers of the imaged primitive features. A constellation algorithm can be used to identify a pattern of primitive features in the first image. A method can include generating an estimated tool state for the tool by using at least one prior tool state from a prior image of the tool or joint data from a robotic actuation system effecting movement of the tool, and using the estimated tool state in the constellation algorithm. A method can include: capturing stereo images for multiple time points; generating an estimated tool state for the multiple time points; and rejecting any incompatible pattern detection using a robust estimation technique, which can be a Random Sample Consensus (RANSAC) technique. A model based image signature can be used in the identification of a primitive feature in an image. A method can include: processing the stereo images so as to identify a natural feature of the tool in both of the images; determine a 3-D position for the identified natural feature; and determine an image-derived tool state by using the 3-D position for the natural feature in combination with the 3-D positional data for the imaged primitive features. A method can include generating an estimated tool state for the tool by using at least one prior tool state from a prior image of the tool or joint data from a robotic actuation system effecting movement of the tool, and using the estimated tool state to reject an incompatible pattern detection. At least one of the primitive feature can include convex or concave spherical reflective surface aligned with a joint axis of the tool and the reflective surface can be defined by a joint structure.

In accordance with another embodiment, a minimally-invasive robotic surgery system is provided. The system includes: a robotic surgical tool having multiple primitive features having know positions on the tool, where each feature includes a spherical reflective surface: a light source oriented to transmit illumination light within a patient body; a stereo image capture device adjacent the illumination source so that the illumination light reflected from the primitive features toward the image capture device substantially aligns with a spherical centers of the spherical surfaces; and a processor coupled with the image capture device and configured for determining a position for the tool by processing stereo images so as to locate the spherical centers of the primitive features by using the reflected light.

A minimally-invasive robotic surgery system can involve a number of options. For example, a system can include a tangible medium that includes machine-readable instructions executable by the processor for processing the stereo images. The processor can be configured to determine a position for the tool by processing the stereo images so as to identify at least one of the multiple primitive features by using specular reflected light. A primitive feature can be aligned with a joint axis of the tool and can include a reflective spherical surface defined by a joint structure. The processor can be further configured so as to determine 3-D positional data for the spherical centers of the imaged primitive features by processing the stereo images. The imaging device can include a stereoscopic endoscope. A spherical reflective surface can include a convex or concave surface.

In accordance with another embodiment, a surgical tool for use with a robotic surgery system is provided. The system includes: a stereo imaging device for capturing stereo images of the surgical tool during use; and a processor coupled with the imaging device for processing the captured stereo images so as to determine image-derived positional information for the surgical tool. The surgical tool includes multiple primitive features with each primitive feature including a spherical reflective surface.

In accordance with another embodiment, an object tracking system is provided. The system includes: an object having multiple primitive features with each primitive feature including a spherical reflective surface; a light source oriented to transmit illumination light toward the object; a stereo image capture device for capturing stereo images of the object, the image device being disposed adjacent the illumination source so that illumination light reflected from a plurality of the primitive features towards the image capture device substantially aligns with spherical centers of the spherical surfaces, the image device outputting image data for the stereo images, and a processor coupled with the image capture device and configured to process the image data so as to: determine 3-D position data for three or more of the imaged primitive features; and determine a position for the tool by processing the 3-D position data.

In accordance with another embodiment, a method for estimating the pose of a surgical tool having three or more substantially corner-less primitive features having known positions on the tool is provided. The method includes: using a stereoscopic endoscope to capture stereo images of three or more of the primitive features, the stereo images including a first image and a second image; extracting at least three primitive feature images from the first image; extracting at least three primitive feature images from the second image; determining correspondences between extracted primitive feature images by using image signatures; using the determined correspondences to determine 3-D positions for at least three of the primitive features; identifying a pattern of extracted primitive feature images that corresponds to a pattern of the tool primitive features; and estimating a pose for the surgical tool by using the identified pattern and the determined 3-D positions.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIGS. 14A and 14B respectively illustrate 2-D markers that can be used for an 8 mm instrument shaft and an 8 mm instrument shaft with the markers, in accordance with embodiments.

FIGS. 15A and 15B respectively illustrate 2-D markers that can be used for a 10 mm (ultrasound) instrument shaft and a 10 mm (ultrasound) instrument shaft with the markers, in accordance with embodiments.

FIGS. 16A and 16B respectively illustrate 2-D markers that can be used for a 5 mm instrument shaft and a 5 mm instrument shaft with the markers, in accordance with embodiments.

FIGS. 17A and 17B respectively illustrate 2-D markers that can be used for an ultrasound transducer and an ultrasound transducer with the markers, in accordance with embodiments.

FIGS. 29A, 29B, 29C, 29D, 29E, 29F, 29G, and 29H illustrate some exemplary approaches that can be used to incorporate positional and/or identification information within a discernible marker, in accordance with embodiments.

FIGS. 30A, 30B, 30C, and 30D illustrate some additional exemplary discernible marker designs, in accordance with embodiments.

DETAILED DESCRIPTION

Figure 1:
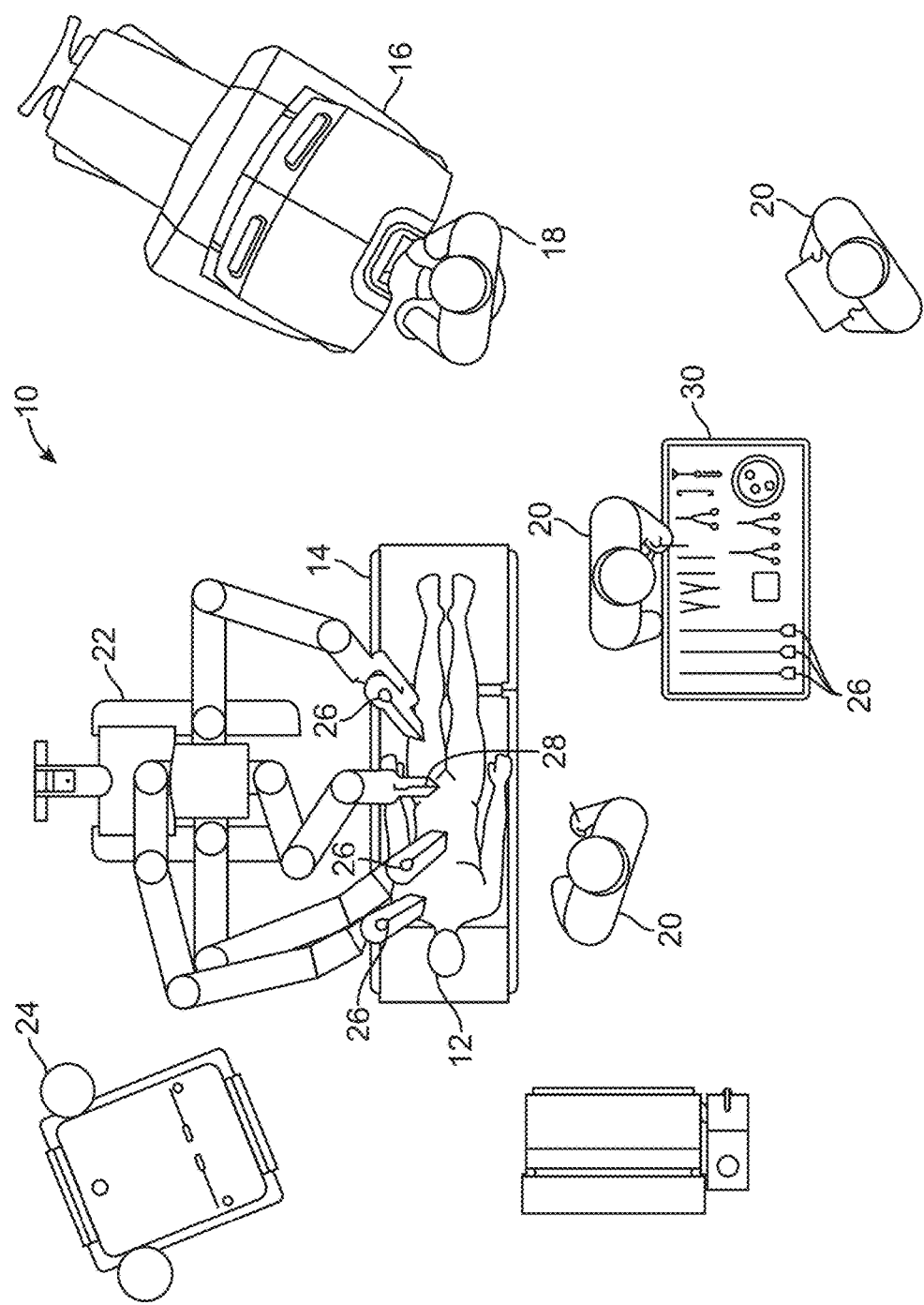
FIG. 1 is a plan view of a minimally-invasive robotic surgery system being used to perform a surgery, in accordance with embodiments.

In accordance with embodiments, improved methods and systems are provided for three-dimensional (3-D) object tracking using image-derived data from one or more object located reference features. Such methods and systems can be particularly advantageous when employed for tracking surgical tools during minimally-invasive robotic surgery.

The following terms are used herein. A "feature" is a general term used to denote whatever useful information can be extracted from an image. A "primitive feature" is used to denote small or simple features that can be extracted locally from an image (e.g., a salient blob, a small circle, a dot, a bar, etc.). A primitive feature is in contrast with a "composite feature", where multiple primitive features are used to create a composite feature. A "marker" is some discernible (typically visible) pattern used for locating an object or computing the pose of an object. A marker can be composed of multiple primitive features. A "tool state" is a general term used to denote any information relating to a tool, such as pose (position and orientation), as well as related information for any articulated parts of the tool or any robotic or positioning system used to manipulate the tool. For example, a tool state can include the pose of the tool, robotic joint parameters of a robotic actuation system used to effectuate movement of the tool, articulated end effector positions, velocity of the tool, acceleration of the tool, forces on the tool, and the like. A "localizer feature" is a feature that can be processed so as to provide positional information for the feature. Multiple primitive localizer features can be processed so as to provide position and orientation (i.e., alignment) information for the rest of the features of a pattern. A "model" is a general term used to refer to any prior knowledge of the physical tool being tracked. This can include a physical model, a virtual model, the locations of the features on the tool and their properties, and the like.

One advantage, for example, of a tool-located reference feature is that it provides at least one feature that can be more easily detected within an image. Some tool use environments, such as minimally-invasive robotic surgery, present challenges to the use of image-derived tool tracking, such as the presence of bodily fluids on the tool and/or the presence of cauterization vapors, which can result in partial or total occlusion of the tool. By configuring a tool to include one or more reference features, the impact of the environment on image-derived tool tracking can be reduced.

Another advantage, for example, is that multiple reference features can be used to define a marker that includes position/orientation information and/or identification information. With sufficient position/orientation information, a 3-D pose (position and orientation) of an object (e.g., tool) can be determined. Position and orientation information can be included within a single marker, or it can be included Within a combination of markers. Identification information can be used to relate an imaged marker Edith associated positional relationship data for that imaged marker and the object. Such identification can be used to distinguish between imaged markers where multiple markers features are used on the object.

Another advantage, for example, is that multiple markers can be employed so as to provide redundancy. For example, a tool can include multiple markers distributed around the tool so as to provide reference features regardless of the particular orientation of the tool during use. Any single marker in a collection of markers can include a number of features so as to provide positional and orientation information for the determination of the 3-D pose of the tool. Any particular marker in a collection of markers can include identification features associated with an identification for the particular marker. The redundancy provided by multiple markers can contribute to a more accurate pose estimation by providing multiple pose estimations that can be averaged so as to reduce random error that may arise during feature localization.

Another advantage, for example, is that redundant features can be employed so as to provide for error checking. For example, a marker can include redundant features defining error-checking data. The error-checking data can be checked for consistency with a identification for the marker so as to validate the determined identification. Additionally, the redundant features can include check sum data, which can be used to guard against misidentification due to occlusion (or non-imaging in general) of one or more marker features. The explicit error-checking mechanism provides confidence in the detection of such markers by reducing the chance of falsely detecting a marker from background clutter or accidental alignment of markers close by to a very, low probability.

A determined 3-D pose can be used to modify a displayed image of the tool in a variety of ways. For example, the displayed image can be modified so that the added reference features are less visually obtrusive, or are "erased" entirely by altering portions of the images located at the reference features.

Minimally-Invasive Robotic Surgery

FIG. 1 provides an appropriate starting point for a discussion of the present invention. FIG. 1 is a plan view illustration of a Minimally-Invasive Robotic Surgical (MIRS) system 10, typically used for performing a minimally-invasive diagnostic or surgical procedure on a Patient 12 who is lying on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot), and a Vision Cart 24. The Patient Side Cart 22 can manipulate at least one removably coupled instrument or tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 so as to orient the endoscope 28. The Vision Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 no longer being used at the time from the Patient Side Cart 22, and replace it With another tool 26 from a tray 30 in the operating room. An illustrative example of system 10 is the da Vinci® Surgical System manufactured by Intuitive Surgical, Inc., Sunnyvale, Calif.

Figure 2:
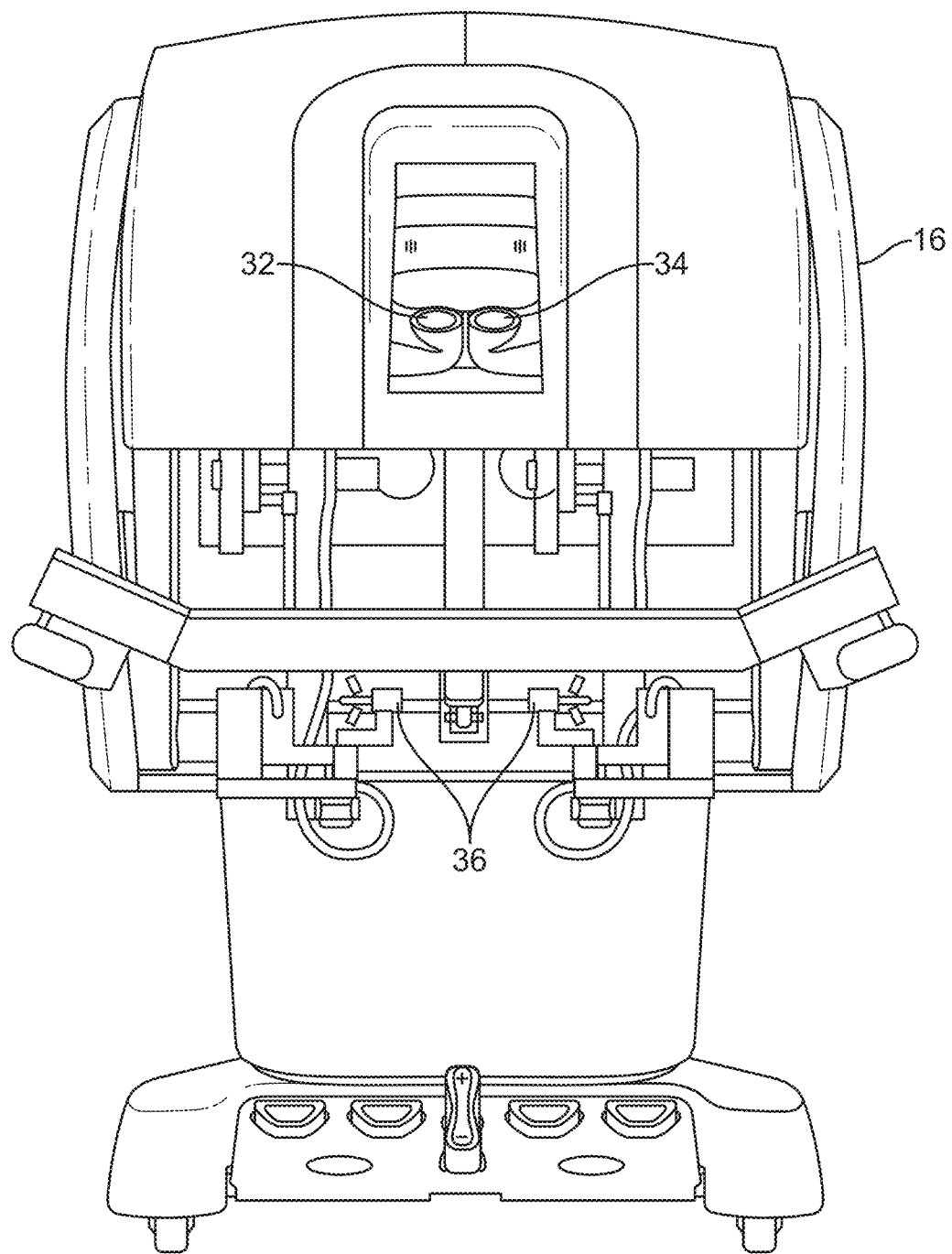
FIG. 2 is a front view of a surgeon's control console for a robotic surgery system, in accordance with embodiments.

FIG. 2 is a front view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more control devices 36, which in turn cause the Patient Side Cart 22 (shown in FIG. 1) to manipulate one or more tools. Preferably, control devices 36 will provide the same degrees of freedom as their associated tools 26 (shown in FIG. 1) so as to provide the Surgeon with telepresence, or the perception that the control devices 36 are integral with the tools 26 so that the Surgeon has a strong sense of directly controlling the tools 26. To this end position, force, and tactile feedback sensors (not shown) are preferably employed to transmit position, force, and tactile sensations from the tools 26 back to the Surgeon's hands through the control devices 36.

The Surgeon's Console 16 is usually located in the same room as the patient so that the Surgeon may directly monitor the procedure, be physically present if necessary, and speak to an Assistant directly rather than over the telephone or other communication medium. However, it will be understood that the Surgeon can be located in a different room, a different building, or other remote location from the Patient, thus allowing for remote surgical procedures.

Figure 3:
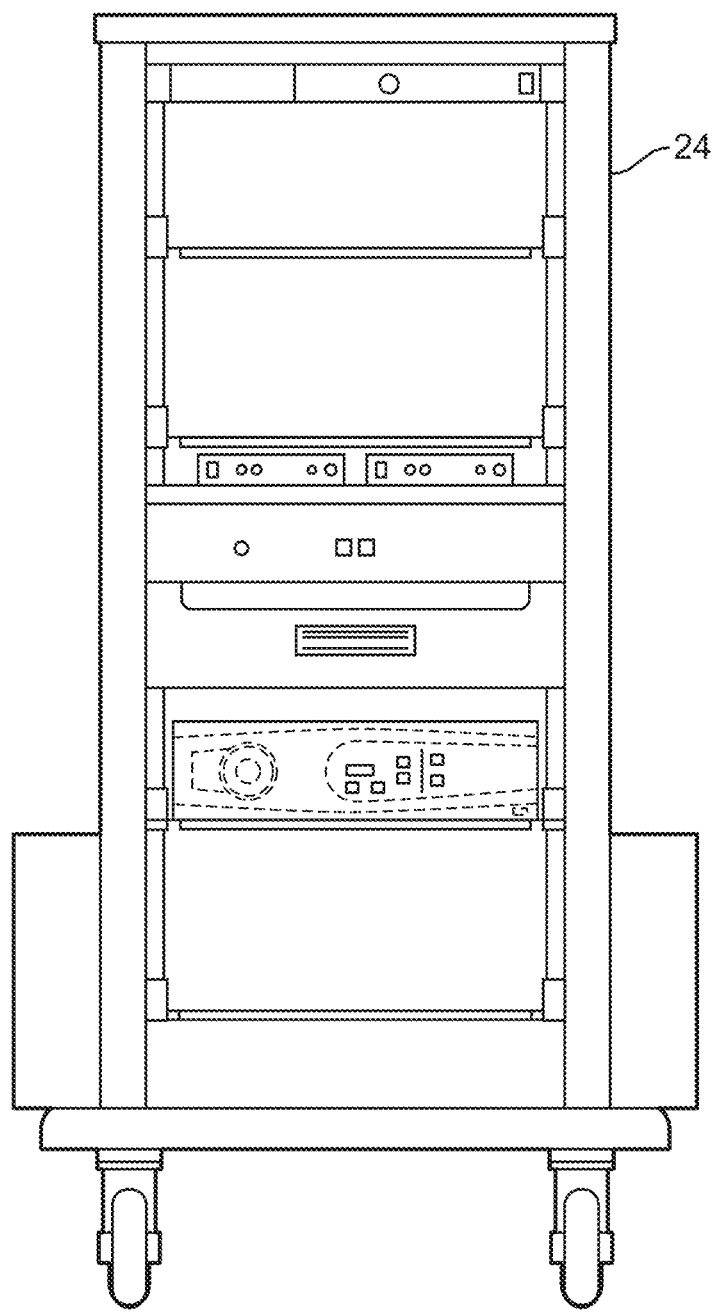
FIG. 3 is a front view of a robotic surgery system vision cart, in accordance faith embodiments.

FIG. 3 is a front view of a Vision Cart 24. A Vision Cart 24 can be coupled with the endoscope 28 and can include a processor to process captured images for subsequent display, such as to a Surgeon on the Surgeon's Console or on any other suitable display located locally and/or remotely. For example, where a stereoscopic endoscope is used, the Vision Cart 24 can process the captured images so as to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters so as to compensate for imaging errors of the image capture device, such as optical aberrations. Exemplary details of some of the possible image processing that can used are described in numerous patents and patent applications assigned to Intuitive Surgical, Inc., including, for example U.S. Pat. No. 7,277, 120 (filed Mar. 7, 2004), the full disclosure of which is included herein by reference.

Figure 4:
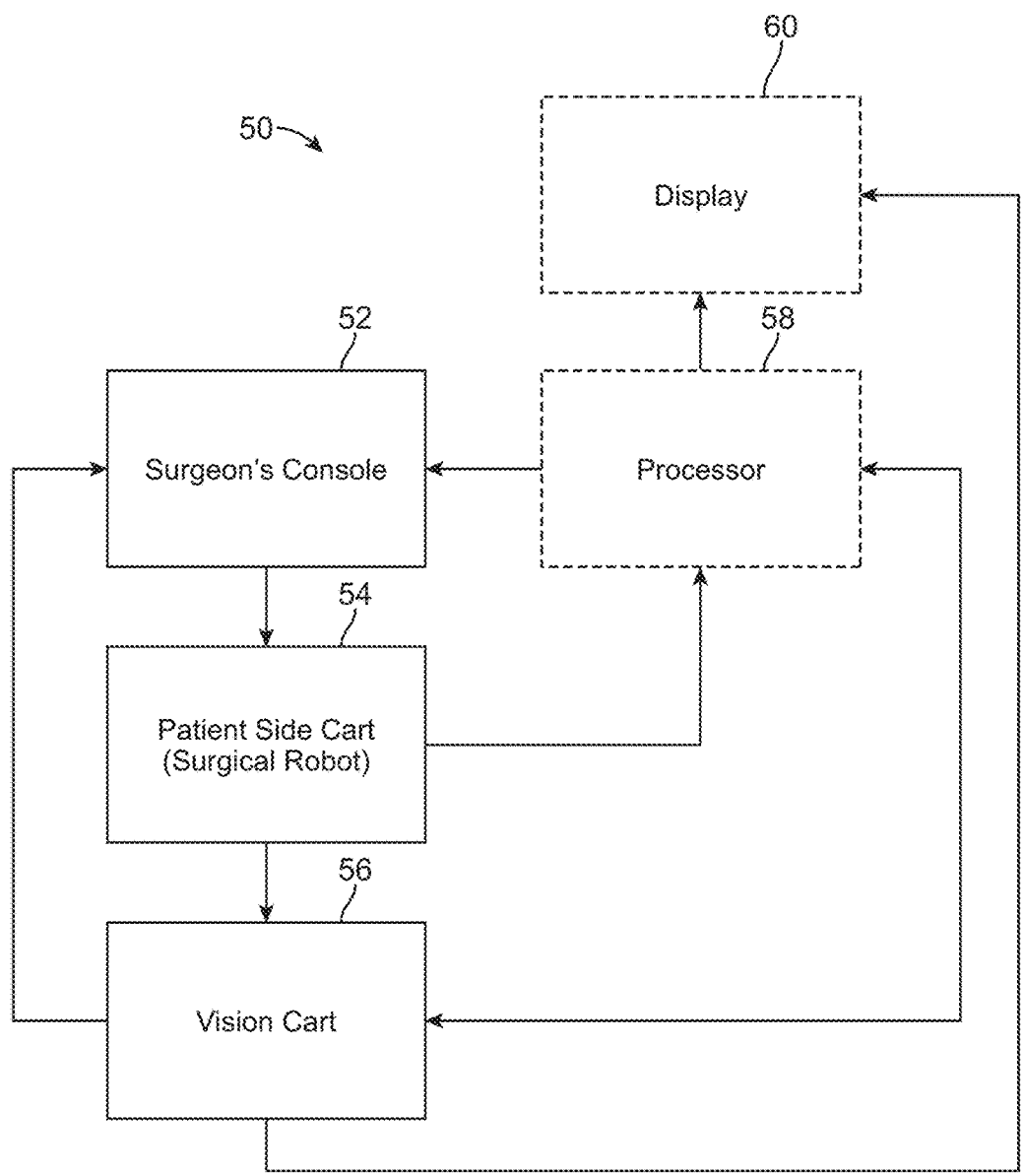
FIG. 4 diagrammatically illustrates a robotic surgery system, in accordance with embodiments.

FIG. 4 diagrammatically illustrates a robotic surgery system 50 (such as MIRS system 10 of FIG. 1), showing communication paths between components. As discussed above, Surgeon's Console 52 (such as Surgeon's Console 16 in FIG. 1) can be used by a Surgeon to control a Patient Side Cart (Surgical Robot) 54 (such as Patent-Side Cart 22 in FIG. 1) during a minimally-invasive procedure. The Patient Side Cart 54 can use an imaging device, such as a stereoscopic endoscope, to capture images of the procedure site and output the captured images to a Vision Cart 56 (such as Vision Cart 24 in FIG. 1). As discussed above, a Vision Cart 56 can process the captured images in a variety of ways prior to any subsequent display. Alternatively, the Patient Side Cart 54 can output the captured images for processing outside the Vision Cart 56. For example, the Patient Side Cart 54 can output the captured images to a processor 58, which can be used to process the captured images. The images can also be processed by a combination the Vision Cart 56 and the processor 58, which can be coupled together so as to process the captured images jointly, sequentially, and/or combinations thereof. One or more separate displays 60 can also be coupled with the processor 58 and/or the Vision Cart 56 for local and/or remote display of images, such as images of the procedure site, or any other related images.

Robotic Surgery Tool Tracking

Figure 5C:
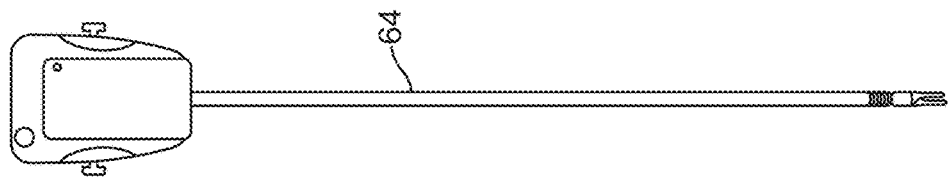
FIGS. 5B and 5C are respective front views of an 8 mm shaft robotic surgery tool and a 5 mm shaft robotic surgery tool, in accordance with embodiments.
Figure 5B:
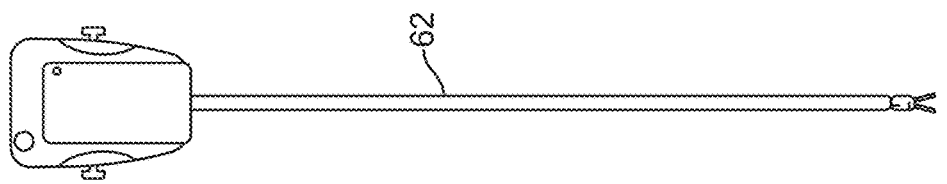
Figure 5A:
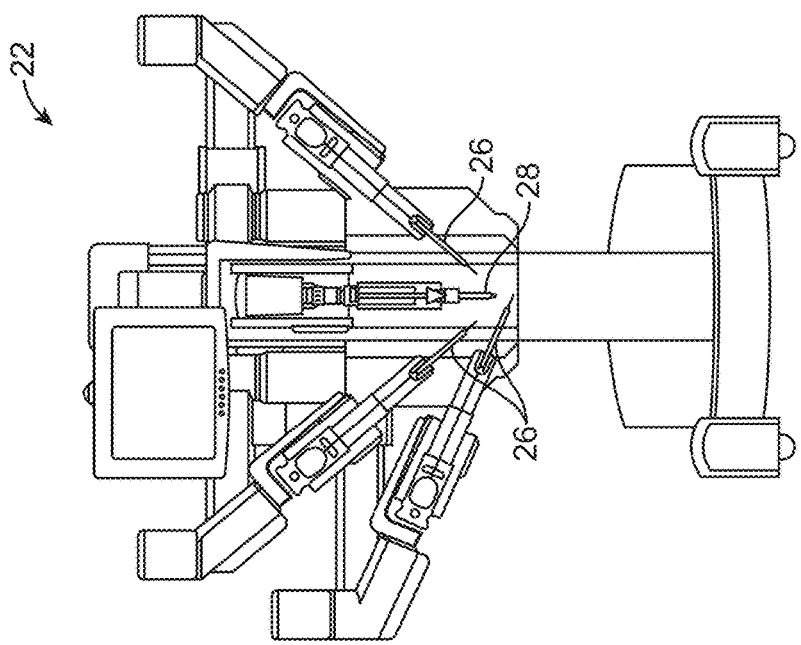
FIG. 5A is a front view of a patient side cart (surgical robot) of a robotic surgery system, in accordance with embodiments.

FIGS. 5A, 5B, and 5C show a Patient Side Cart 22, an 8 mm shaft surgical tool 62, and a 5 mm shaft surgical tool 64, respectively. Surgical tools 62 and 64 are examples of surgical tools 26. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 (e.g., the end effectors 66) can be positioned and manipulated through incisions in the patient so that a kinematic remote center is maintained at the incision so as to minimize the size of the incision required. Images of the surgical site can include images of distal ends of the surgical tools 26 when they are positioned within the field of view of the imaging device 28.

Figure 6:
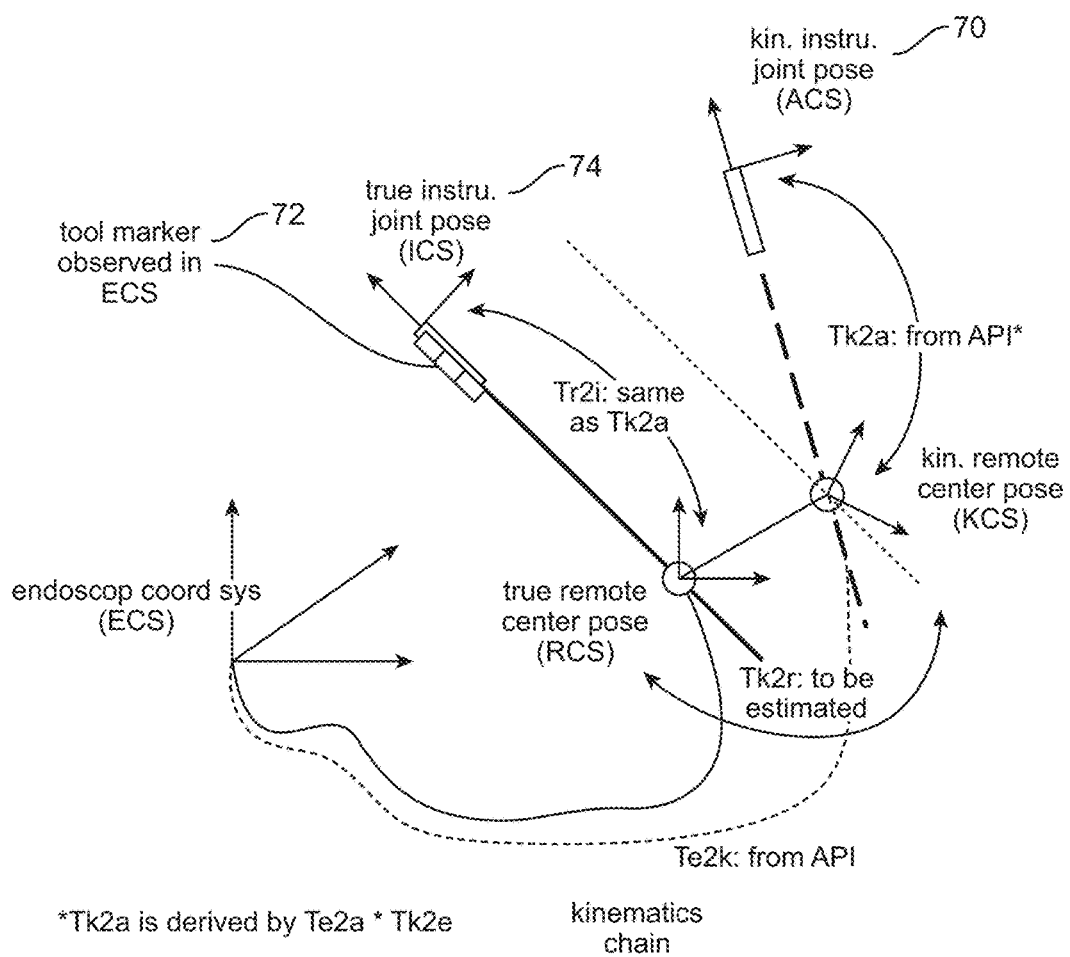
FIG. 6 diagrammatically illustrates relative differences between a kinematics-estimated tool pose, an image-derived estimated tool pose, and a true tool pose, in accordance with embodiments.

FIG. 6 diagrammatically illustrates relative differences between a kinematics-estimated surgical tool pose 70, an image-derived estimated surgical tool pose 72, and a true surgical tool pose 74. As discussed above, accurate information of a tool's 3-D pose is important for a number of image-guided surgical and user-interface applications. When kinematic joint sensor data is used to estimate the tool's 3-D pose, a significant amount of error can be introduced. Although many sources of error exist, such as random sensor noise, a predominant portion of this error can be attributed to offset error, which arises due to fixed differences between a kinematic joint's true position and a kinematic joint's indicated position as indicated by kinematic joint sensor data. Offset errors in kinematic joints located farther away from the tool's distal working end typically contribute more to the total offset error than joints located closer to the tool's distal working end. As a result, a kinematics-estimated pose 70 can deviate significantly from a true pose 74 for the surgical tool. For example, a kinematics-estimated tool pose for an exemplary surgical robot may differ from a true pose for the tool by up to 10 to 15 mm on a well-calibrated system, and even more if the system has not been recently and/or accurately calibrated. As a result, it can be advantageous to use non-kinematics based methods to obtain more accurate tool pose estimates, which can be used to determine a positional correction for use in correcting the kinematics estimates.

An image-derived tool pose estimate 72 can be significantly more accurate than a raw kinematics-estimated tool pose 70. This increased accuracy is diagrammatically illustrated in FIG. 6 by the relatively small positional difference between the image-derived tool pose 72 and the true tool pose 74 shown. However, an image-derived tool pose 72 mall be available at a significantly lower rate (e.g., less than or equal to approximately 30 frames per second) than a raw kinematics-estimated tool pose (e.g., updated at an approximately 1333 Hz rate) due to a number of factors, such as required image processing times, and at certain times it may not be available at all where the tool is outside the view of the imaging device, or is occluded for some reason, such as by patient tissue, by patient bodily fluids, and/or by opaque or translucent vapors due to cauterization, or the like.

Figure 7:
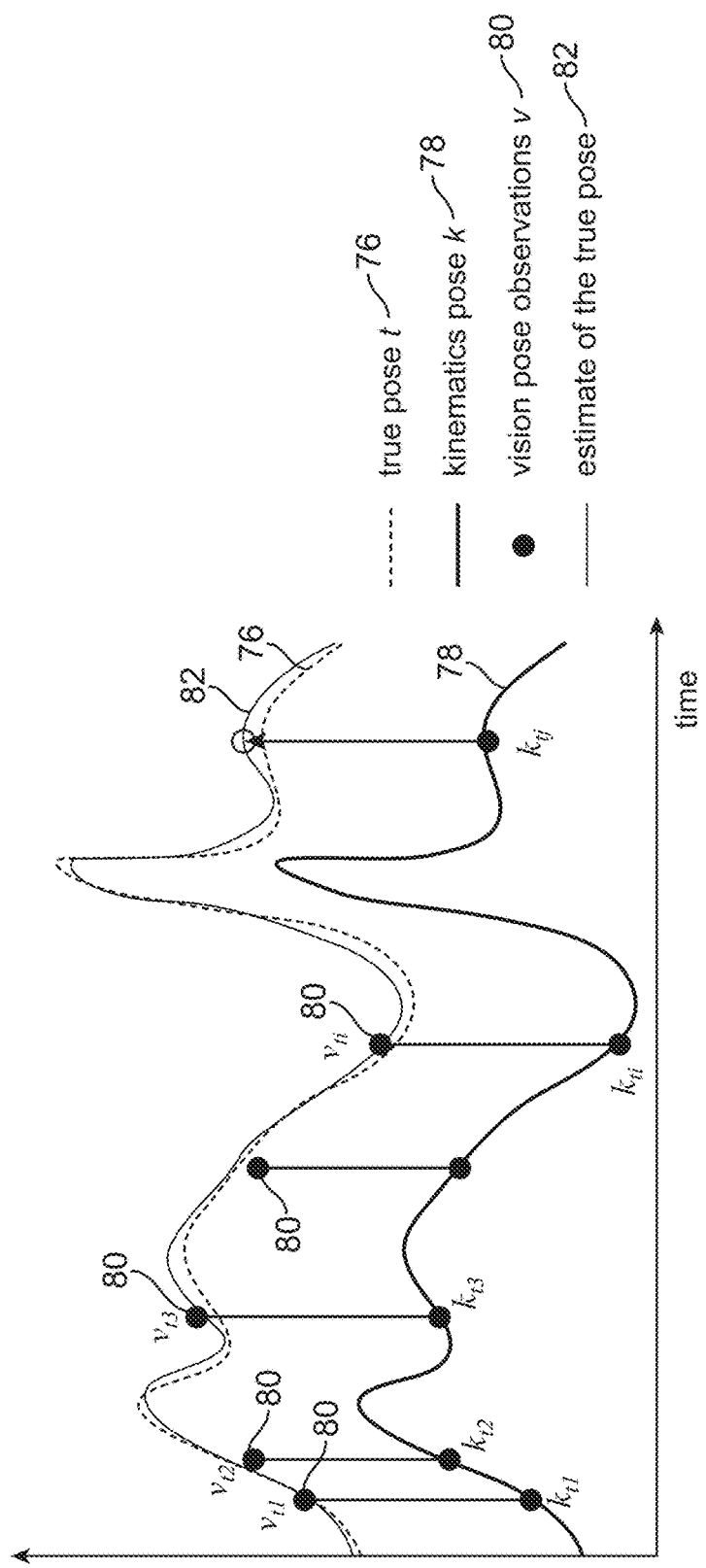
FIG. 7 diagrammatically illustrates variations with time of a raw kinematics-estimated tool pose, an image-derived estimated tool pose, an estimate of the true tool pose, and a true tool pose, in accordance with embodiments.

FIG. 7 diagrammatically illustrates variations with time between various estimated poses and the true pose 76 of a tool. As shown, a raw-kinematics estimate 78 for a pose for the tool can deviate significantly from the true pose 76. As discussed above, a predominant portion of this deviation may be associated with a fixed offset error, which is illustrated by way of the substantially constant offset between the raw-kinematics estimate 78 and the true pose 76. Due to the relatively high rate of availability of kinematics sensor data, the raw kinematics-estimated pose 78 can be available at a high rate, such as 1333 times per second. In contrast, an image-derived pose estimate 80 may be available at a lower rate, but can be relatively accurate. Advantageously, a combination of kinematics-estimated poses and image-derived estimated poses can be used to determine a true pose estimate 82, which may track the true pose 76 relatively well. Details of the use of a combination of raw kinematics-estimated poses and image-derived estimated poses for the determination of a true pose estimate 82 are described in numerous patents and patent applications assigned to Intuitive Surgical, Inc. including, for example in U.S. Pat. App. Pub. No. 20006/0258938 A1 (filed May 16, 2005), the full disclosure of which is included herein by reference.

Figure 8:
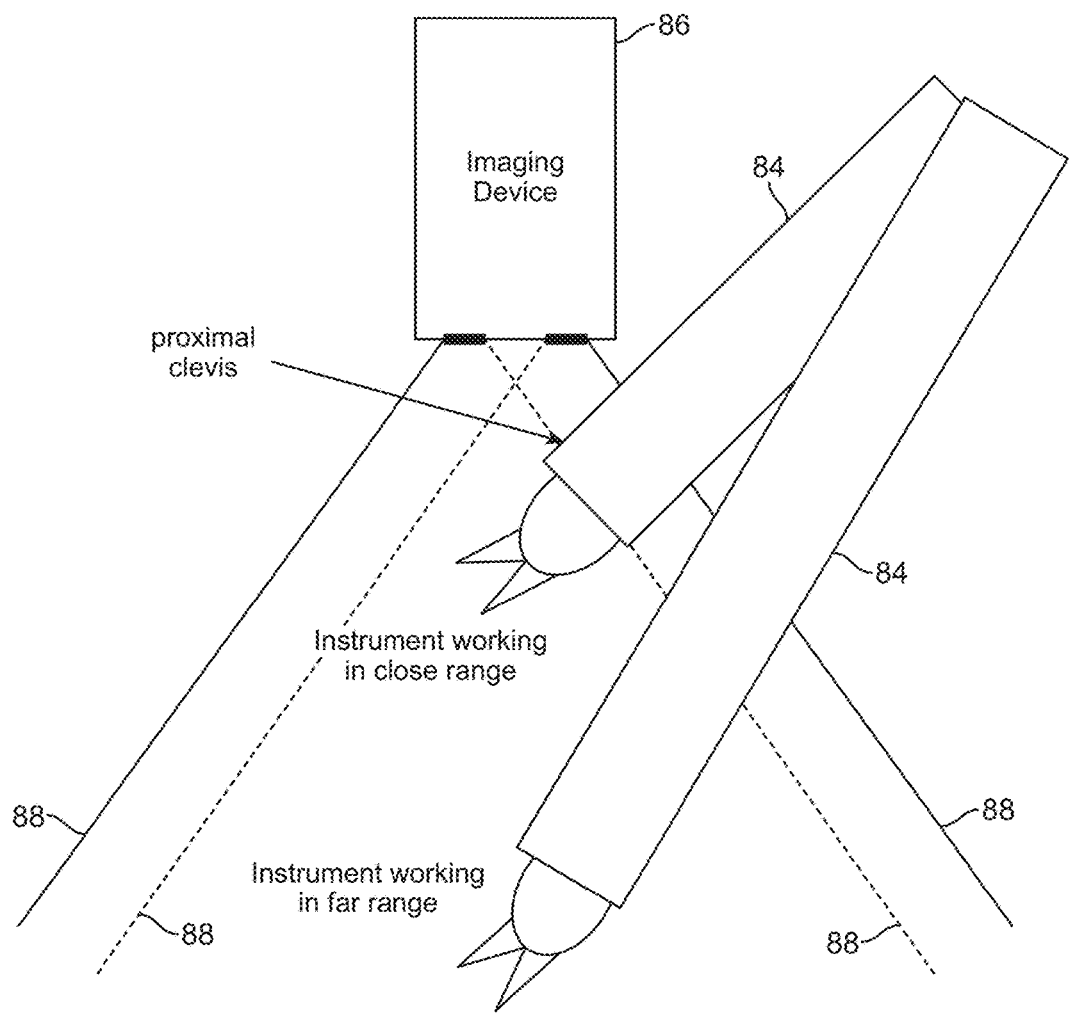
FIG. 8 is a diagram illustrating surgical instruments working in close and far range to a stereoscopic imaging device.

FIG. 8 illustrates variations that can occur in the portion of a surgical instrument 84 (e.g., the toot 26) that may be within view of an imaging device 86, such as the stereoscopic endoscope 28. The imaging device 86 can include two overlapping fields of view 88 used to capture images of the procedure site and any, surgical instrument portion within a field of view 88. When the instrument 84 is working in far range from the imaging device 86, a greater portion of the surgical instrument 84 may be included within the captured image, but the relative size of any imaged tool feature(s) will be smaller as compared with the field of view as a whole. When the instrument 84 is working in close range to the imaging device 86, a relatively smaller portion may be included within the captured image, but the relative size of any imaged tool feature(s) will be larger as compared with the field of view as a whole.

Figure 9:
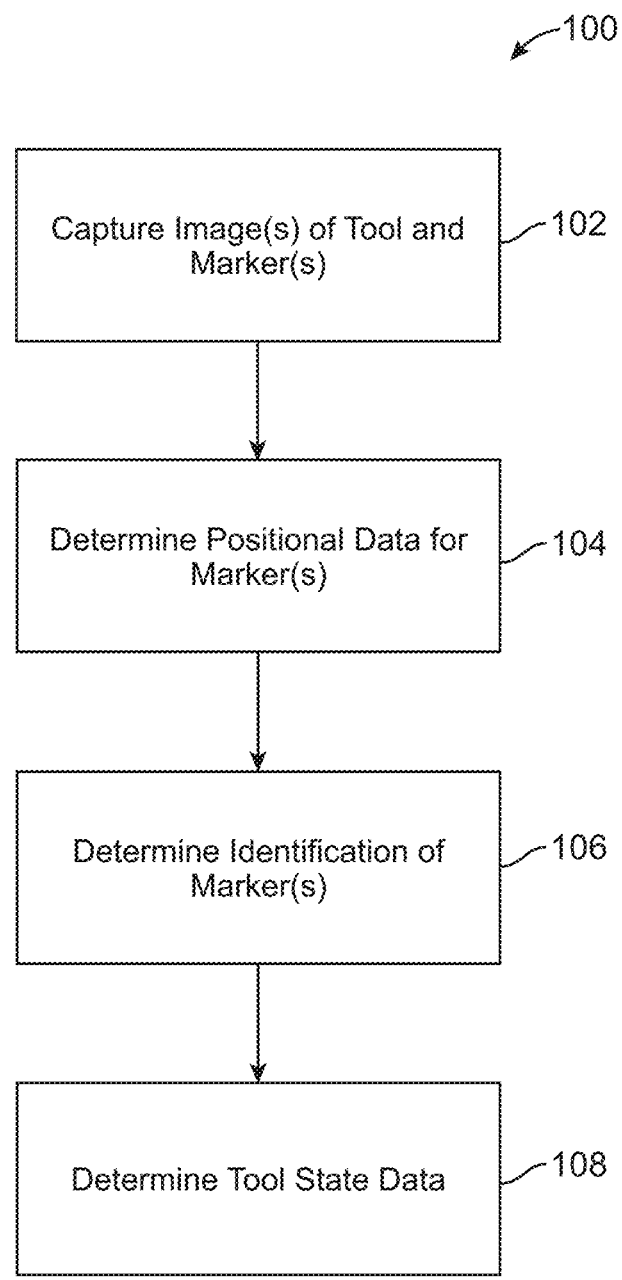
FIG. 9 is a flow diagram of a tool tracking method employing imaging of markers, in accordance With embodiments.

FIG. 9 is a flow diagram of a tool tracking method 100 employing imaging of one or more markers attached to a tool. As will be described in more detail below, a tool, such as the tool 26, can include one or more markers so as to provide features that can be imaged and processed to provide an image-derived tool pose estimate. In step 102, one or more images of the tool and marker are captured. The captured image(s) can be a single image obtained through the use of a mono-vision imaging device or stereo images obtained with a stereo-vision imaging device, such as a stereo endoscope. In step 104, the captured image(s) are processed so as to determine positional data associated with one or more marker(s). The positional data can include the location of one or more marker features within the image(s). At least where two or more markers having different identifications are used on one or more surgical tools, the image can be processed in step 106 to determine the identification of one or more of the markers. As will be described below in more detail, a marker can contain one or more identification features that can be imaged and subsequently processed to determine the identification of the marker. In step 108, the positional data and any identification can be used to determine tool state data, such as the tool's 3-D pose. Additional information, such as relative positional data between a marker and the tool can be used during the determination of tool state data. For example, relative 3-D pose offset data (offset position and offset orientation) between the 3-D pose of the marker and the 3-D pose of the tool can provide the relative positional data.

The tool state data determined in step 108 can be rejected if it is insufficiently consistent with an expected tool state data range. For example, an estimated 3-D pose for the tool can be generated by using a prior image of the tool or joint data from a robotic actuation system effecting movement of the tool. This estimated 3-D pose can be compared with the tool state data determined in step 108 so as to verify that then are consistent with each other. Any inconsistency can be evaluated to determine whether to reject the determined tool state data as being an outlier.

Figure 10:
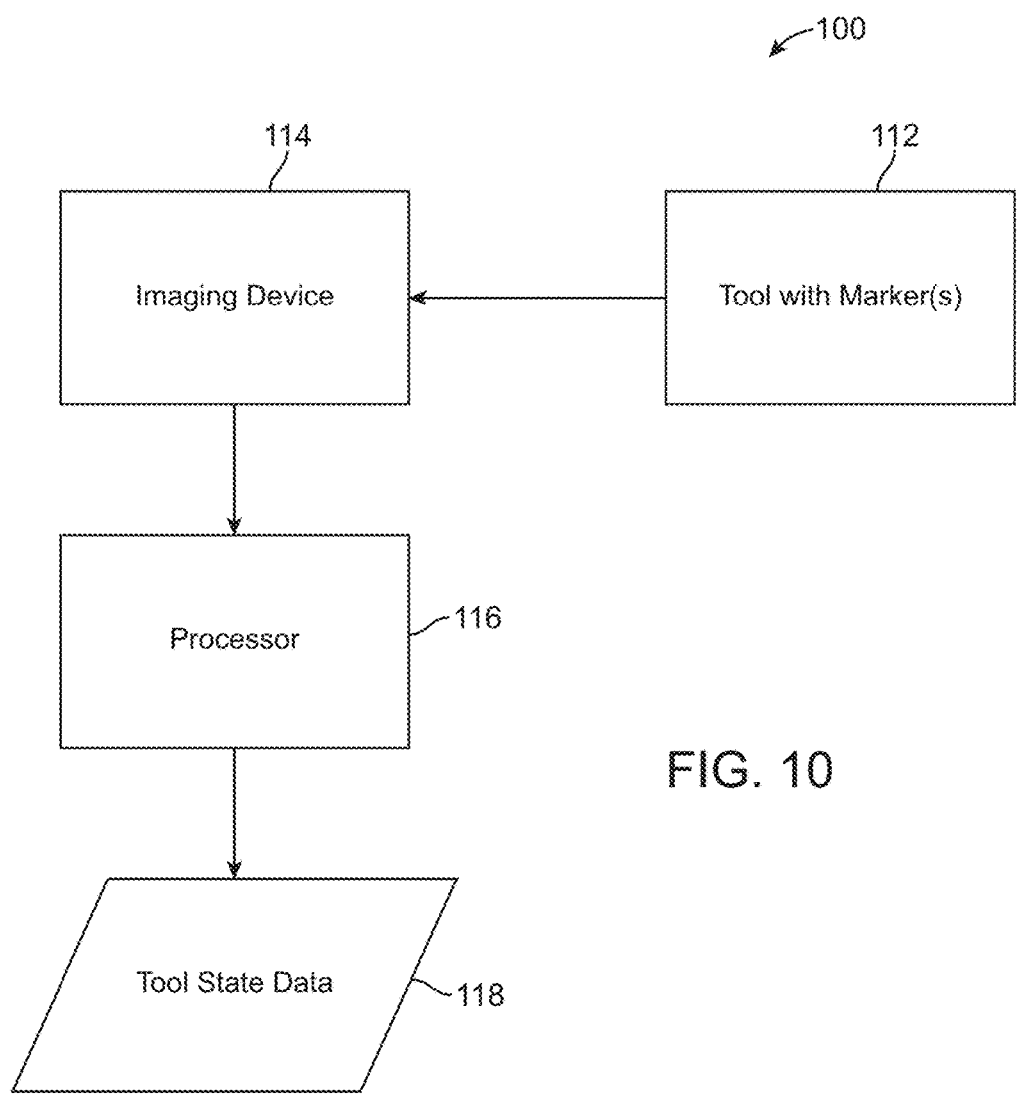
FIG. 10 diagrammatically illustrates a system for tracking tools with markers, in accordance with embodiments.

FIG. 10 diagrammatically illustrates a system 110 for tracking a tool with marker(s) 112. The system includes at least one tool with a marker(s) 112, similar to the tool 26. An imaging device 114, such as the stereoscopic endoscope 28, is used to capture one or more image(s) of the tool with marker(s) 112. The imaging device 114 is coupled with a processor 116 and transfers image data to the processor 116 in response to imaging the tool with marker(s) 112. The processor 116 is configured to process the received image data so as to generate tool state data 118, which can include an estimated 3-D pose for the tool with marker(s) 112.

Figure 11:
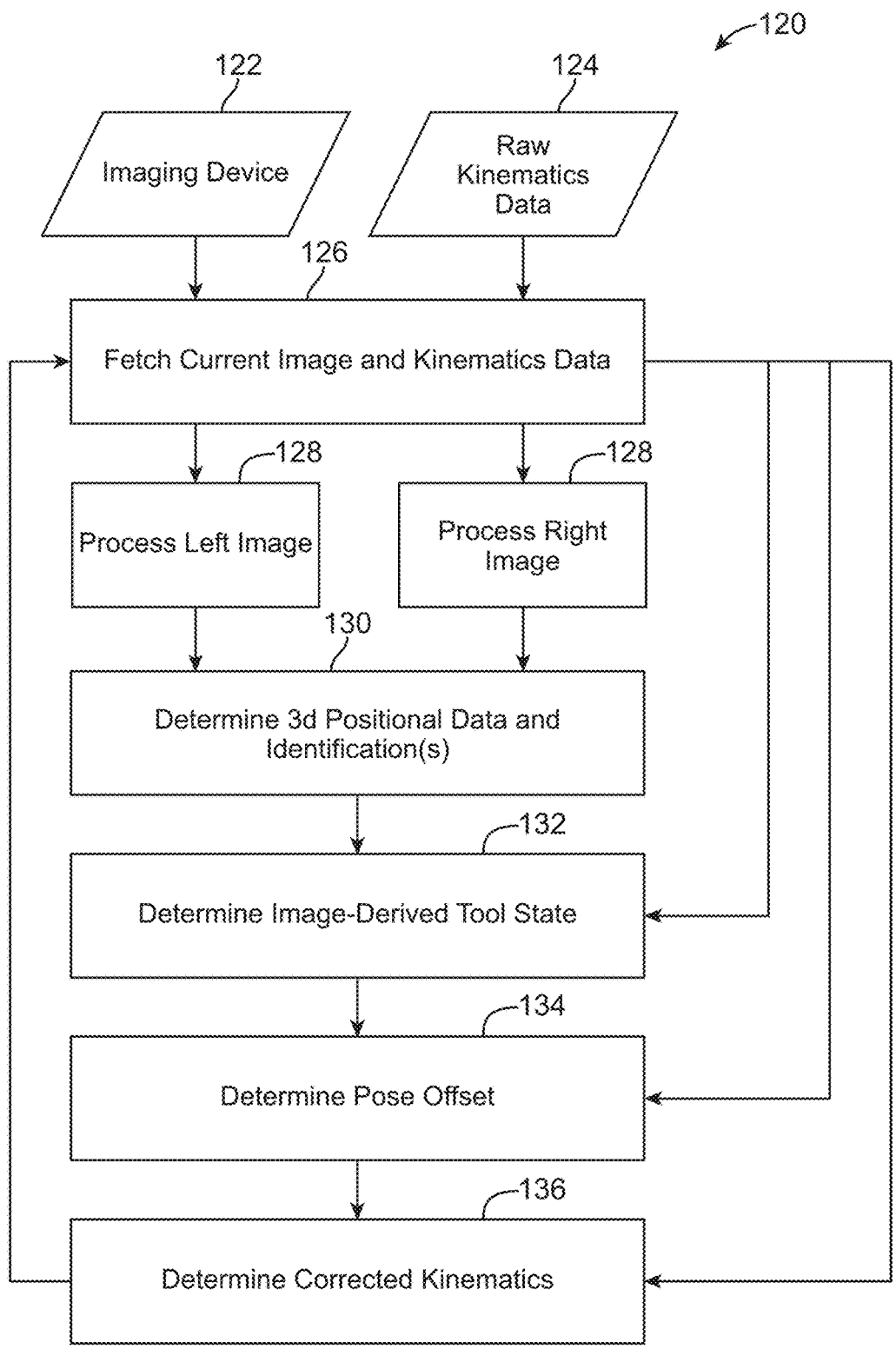
FIG. 11 is a flow diagram of a tool tracking method for determining a tool state showing steps for processing stereoscopic images of markers and kinematics data to generate a corrected-kinematics estimated tool state using an image-derived pose offset, in accordance with embodiments.

FIG. 11 is a flow diagram of a tool tracking method 120 for determining a tool state showing steps for processing stereo images of markers and raw-kinematics data to generate a corrected kinematics-estimated tool state using an image-derived 3-D pose offset, in accordance with an embodiment. Because of the higher update rate of the joint sensor data used to generate an estimated tool state from raw kinematics data 124 as compared to an image-derived estimated tool state, an image-derived pose offset can be combined with an estimated tool state from raw kinematics to generate a corrected kinematics estimated tool state. In this ways, a series of corrected kinematics estimated tool states can be generated using a single pose offset combined With a corresponding series of estimated tool states from raw kinematics data 124. The pose offset can be updated over time in response to new image data 122.

The determination of a pose offset starts in step 126 with the acquisition of image data of the tool with marker(s) and corresponding raw kinematics data 124 for the tool with marker(s). As shown the image data 122 can include left image data and right image data, but it should be understood that a single image of one or more marker features can be processed so as to generate image-derived positional information useful in generating a pose offset. For example, the location within an image of a single marker feature can be compared with an expected location within the image for the single marker feature so as to generate a one-dimensional (1-D) correction for the previous pose offset. Where a single image contains four non-collinear features, the locations of the four non-collinear features within the image are sufficient to determine an image-derived 3-D pose for the tool. Where stereo images contain three non-collinear features, the locations of the three non-collinear features Within the stereo images are sufficient to determine an image-derived 3-D pose for the tool. The raw kinematics data 124 can include basic sensor data, such as kinematic joint position parameters, and/or can include a current raw kinematics-derived tool state.

In step 128, the left image and the right image are processed so as to detect marker features. The position of the marker(s) feature(s) within the left image and the position of the marker(s) feature(s) within the right image are used in step 130 to generate 3-D coordinates for the marker(s) feature(s). For details of stereo triangulation, see for instance chapter 12 of R. Hartley, and A. Zisserman, "Multiple View Geometry in Computer Vision," Cambridge University Press, 2000. As will be described in more detail below with respect to certain embodiments, with some markers having an identification, a marker can include at least one identification feature that can be processed to determine the identification of the marker.

In step 132, the 3-D coordinates for the marker(s) features (s) can be processed in combination with any identification (s) of markers(s) so as to determine an image-derived tool state. Although images of a number of markers can be used to provide sufficient pose information for determining a 3-D pose for the tool, it can be advantageous for a single marker to contain a sufficient number of features for determining a 3-D pose for the tool. Additionally, it can be advantageous for each marker on a tool to have an identification that differs from neighboring markers. With such a marker, an image-derived tool state can be determined by determining the 3-D pose of the marker, determining the identification of the marker, and using data regarding how the identified marker is positioned and oriented on the tool. It is appreciated that variations of this approach can be used. For example, features from a combination of markers can be combined to determine the 3-D pose of the combination of markers, which can be combined with data regarding how the features from the combination of markers are positioned and oriented on the tool. During this process, a corrected kinematics estimated tool state (from a previously determined pose offset) can be compared against the image-derived estimated tool state so as to reject any image-derived estimated tool states that differ too much from the corrected kinematics estimated tool state.

In step 134, the pose offset is determined so that it can be combined with a raw kinematics data 124 estimated tool state to obtain a corrected-kinematics estimated tool state. It is appreciated that a variety of approaches malt be used to determine the pose offset. For example, the pose offset can be calculated as a difference between an estimate of the true tool pose (shown in FIG. 7) and a corresponding raw kinematics data 124 estimated tool state for substantially the same point in time. As a further example, the pose offset can be calculated as a difference between an image-derived estimated tool state and a corresponding raw kinematics data 124 estimated tool state for substantially the same point in time.

In step 136, a corrected-kinematics based tool state is determined. As discussed above, a single pose offset can be used to correct one or more raw kinematics data 124 based tool states so as to compensate when raw kinematics data 124 based tool states are available at a higher rate as compared to image-derived tool states. The corrected kinematics can then be provided back to the start of the process (step 126), where the "fetched" current image and kinematics data can include image data, raw kinematics data, and the current pose offset and/or corrected-kinematics data.

Marker Design

A goal in the use of tool markers is to provide a level of robustness and confidence with regard to an image-derived tool state that is difficult to achieve without the use of markers, especially for a critical application such as image-guided robotic surgery. As such, in an embodiment, a marker design: (i) provides sufficient constraint for tool pose estimation; (ii) is distinguishable under various realistic conditions (e.g., viewpoint, lighting) and under various realistic backgrounds; (iii) works with different operational ranges of the tool; (iv) is resilient and/or robust to partial occlusions; (v) is visually acceptable; (vi) is easily manufactured; (vii) is compact enough to allow the use of multiple markers within the space provided (e.g., enough to supply a sufficient level of redundancy), and (viii) can be extracted by an image analysis algorithm.

One-dimensional (1-D) and two-dimensional (2-D) markers can provide a number of advantageous aspects. These include: (i) the use of separate localizer and identification features that support more efficient detection and parsing; (ii) the use of explicit coding schemes for primitive feature locations; (iii) the use of explicit error checking and error correction; (iv) the ability to create a large number of different patterns; (v) the use of a compact marker with dense information; and (vi) the use of a "hypothesize and test" detection algorithm framework, which scales very well with the total number of marker patterns.

Two-Dimensional Marker Designs

Figure 12A:
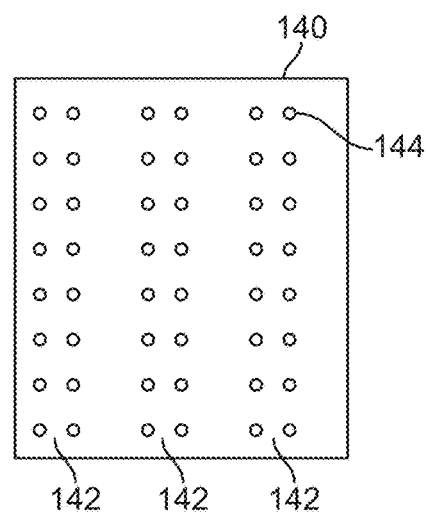
FIG. 12A diagrammatically illustrates a marker pattern that can be used on a surgical instrument to provide additional reference points, in accordance with embodiments.
Figure 12B:
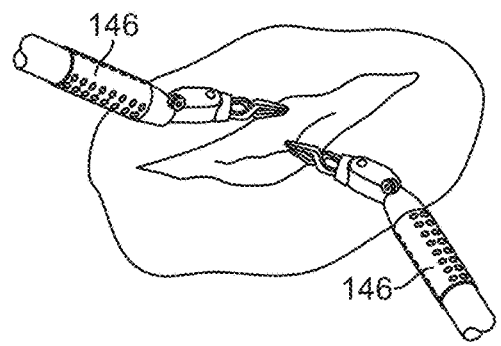
FIGS. 12B and 12C are images of surgical instruments with the marker pattern of FIG. 12A during a minimally-invasive robotic surgery, in accordance with embodiments.
Figure 12C:
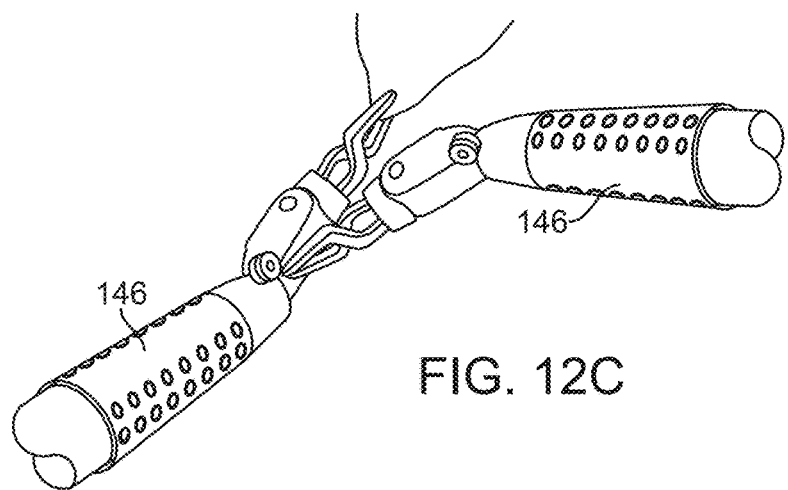

FIGS. 12A, 12B, and 12C illustrate a marker design 140, tools 146 employing the marker design 140 operating at a far range from the imaging device, and a tool employing the marker design 140 operating in close range to the imaging device, respectively. The marker design 140 of FIG. 12A includes three groups of identical patterns 142 that can be placed at 120-degree intervals around a tool shaft. Each pattern 142 has 16 circles in 8 rows and 2 columns on a yellow background. Each pattern 142 can be aligned with the longitudinal axis of a tool shaft so that all of the center points of the 16 circles reside on a single plane. The two columns of circles 144 are spaced relatively closer as compared to the spacing between each pattern 142. This differential spacing, combined with a corrected-kinematics estimated tool state, can be used to identify, the specific pattern 142 in an image. Since the three patterns 142 are arranged around a tool at 120-degree intervals, there may be a sufficient differential between identical images of the overall marker 140, given the inherent level of accuracy of a corrected-kinematics estimated tool state, to discriminate between imaged patterns 142. Marker 140 provides an example how marker features, such as the identical patterns 142 shown, can be arranged so as to present features that can be imaged so as to determine a tool state. Drawbacks of this marker design include: (i) the yellow background is very bright under surgical illumination and appears intrusive; (ii) although the marker 140 covers the end of the instrument shaft, in most cases it is not fully visible during surgery; (iii) there is a need to rely on the assumption that the maximum error in an estimated tool roll angle is less than 60 degrees to associate the image observation With one of the three patterns 142; and (iv) it is difficult to add more markers on another part of the instrument since the markers are difficult to differentiate.

Figure 13A:
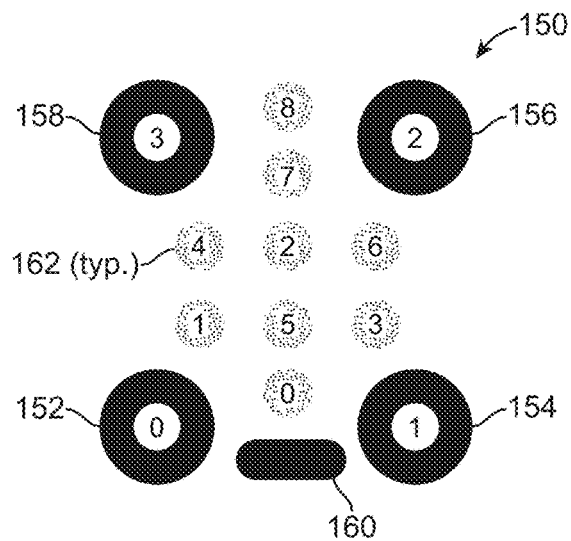
FIGS. 13A, 13B, and 13C illustrate versions of a 2-D marker, in accordance with embodiments.

FIGS. 13A. 13B, and 13C illustrate three embodiments of a 2-D marker 150, 170, 190 that can be used on a tool for tracking the tool's state. A 2-D marker includes primitive features arranged in two dimensions. Some of the features can serve as localizer features, and the other features can serve as identification features. Localizer features provide positional or orientation information to determine pose/alignment of the marker, and the identification features are used to differentiate different markers. The identification features can follow a certain coding scheme and can include redundant information for error checking and/or correction. By using compact 2-D markers, multiple markers can be arranged in different ways to fit the geometric shapes of different tools. The markers can also be arranged at different locations on the tool shaft to cope with different operational ranges. The markers can also be used to estimate the roll of the tool or instrument. Compared to multiple 1-D patterns stacked together, a 2-D marker pattern may advantageously provide better information compactness and location.

These 2-D self-discriminative markers have been designed to meet a number of considerations. The size of the markers has been selected to be as small as possible given the constraint of image resolution. These 2-D markers do not rely on a specific color, because color can be an unreliable feature due to dependence on lighting and white balance. Additionally, some colors can be visually intrusive. These 2-D markers were designed to include features that could be reliably detected in images, because some features are easier to detect than others.

Figure 13B:
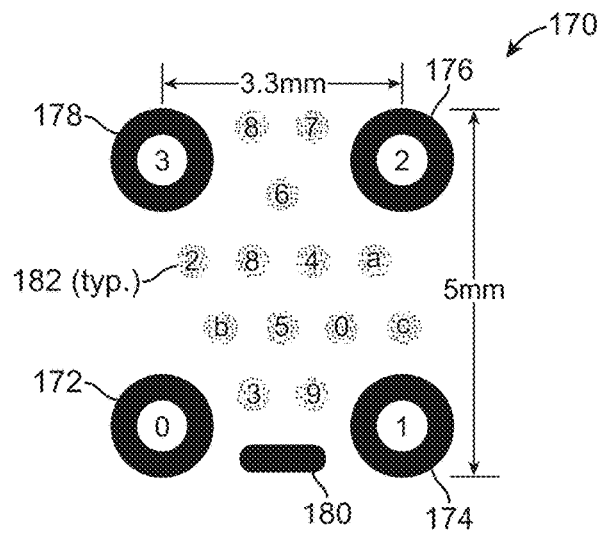
Figure 13C:
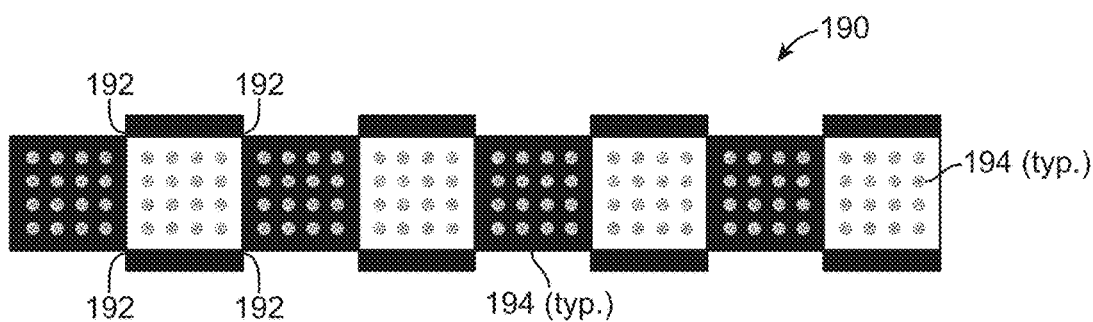

The above considerations resulted in designs for these 2-D markers that included certain design features. For example, these 2-D markers were designed to include localizer shapes (the black circles 152, 154, 156, 158; 172, 174, 176, 178; the black bar 160; 180; and the saddle points 192) and a number of information bits or identification features (nine gray dots 162 in FIG. 13A, thirteen gray dots 182 in FIG. 13B, and the 16 dots 194 in FIG. 13C). (The numbers in the circles and dots in FIGS. 13A and 13B are used for convenience of reference only.) A circle was chosen as a localizer shape because its topology (a dark blob inside a bright blob, or vice versa) is invariant to view point and it usually does not appear in the background. Other such features include certain corners, especially a saddle point 192 as shown in FIG. 13C. Although the marker designs do not restrict how the information bits 162, 182, 194 (identification features) are used, they can be divided into data and error checking bits. The presence or absence of the dots corresponding to data bits can be used to designate a number of unique codes (or identifications). The presence or absence of the gray dots corresponding to error checking bits can be used to validate a code or identification determination. The size of the marker patterns 150, 170, 190 were selected considering a desired working distance range for minimally-invasive robotic surgery. However, it is appreciated that if the instrument usually works closer or farther away from an imaging device, the size of the pattern could be made smaller or larger accordingly. Although the markers 150 and 170 shown in FIGS. 13A and 13B include a white background and dark features, as can be seen in subsequent figures, a dark background with white features was selected based on clinical feedback on the visual experience. However, it is appreciated that a white background and dark features can also be used.

When placed on the surface of an instrument of a certain diameter, the 3-D geometry of the pattern (the 3-D coordinates of all the circles and dots in a local coordinate system) is fixed and known. If a single image is used to provide 2-D coordinates, coordinates of four points are sufficient to determine the pose of the marker (and hence the tool). If stereo images are used to provide 3-D coordinates, coordinates of three points are sufficient to determine the pose of the instrument. Accordingly, the design of these 2-D markers 150 and 170 includes four circles, thereby providing a sufficient number for either single image or stereo image processing. The dots can also be used for object pose estimation. Also, although the markers can be placed on a tool in any number of different orientations, it is presently preferred that the markers be placed so that the vertical direction aligns with the instrument axial direction.

The marker designs 150 and 170 of FIGS. 13A and 13B represent two separate design versions, with the design version of FIG. 13B representing an improved version after experiments. Although the overall size of the pattern did not change, a number of differences exist. The number of information bits 162 and 182 (or identification features) was increased from nine to thirteen, which effectively increased the number of unique patterns. The number of columns for the information bits 162 and 182 increased from three to four, which provided for a more efficient use of limited space. Because it was observed that many typical viewing directions in robotic surgery led to more severe foreshortening of the tool image in the axial direction than in the lateral direction, the pattern of FIG. 13B includes larger vertical spacing between the information bits 182 than horizontal spacing. The rows of the information bits 182 in the pattern of FIG. 13B are also interleaved, which also helps alleviate foreshortening relative to a non-interleaved pattern. The diameter of the information bits 162 and 182 (dots) and the thickness of the circles were also reduced, which resulted from an observation that the testing vision system usually dilated bright features. Accordingly, the features were made thinner to maintain isolation.

The information bits 162, 182, 194 in these 2-D patterns can be used in a variety of ways, such as using a number for identification bits and the remaining number for error checking/correction bits. The partition between identification bits and error checking/correction bits and their arrangement are flexible and can be determined based upon the specific application requirements. One may use fewer numbers of bits for error checking/correction if the imaging situation is less challenging. In one approach, the thirteen information bits of the marker of FIG. 13B are separated into six bits used to carry identification information (resulting in 64 unique codes), with the remaining seven bits used for error checking/correction. Among the seven error checking/correction bits, six can be set to be the inverse of the identification bits, and the remaining bit can be used as checksum data. The rationale for this approach is to always ensure that there are six or seven bits that are physically present in a pattern (i.e., they are set to one). This avoids an all zero (all blank) pattern as a valid code and provides alternative features that can be used to provide positional information for pose estimation if required. It is appreciated that the above described coding scheme may not be optimal from a coding theory point of view. Coding schemes having more Hamming distance between valid code words are preferred. It is also appreciated that there may not be a distinction between identification bits and error-checking bits from a coding theory point of view. Redundancy results from the fact that valid code words only occupy a portion of the code space (i.e., the Hamming distance between two valid code words is greater than 1).

FIGS. 14A. 14B, 15A, 15B, 16A, 16B, 17A, and 17B show four different multiple marker patterns by themselves and as applied to specific robotic tool instruments. FIGS. 14A and 14B respectively illustrate 2-D markers that can be used for an 8 mm (diameter, same convention for other instruments) instrument shaft and an 8 mm instrument shaft with the markers. FIGS. 15A and 15B respectively illustrate 2-D markers that can be used for a 10 mm instrument shaft and a 10 mm instrument shaft with the markers. FIGS. 16A and 16B respectively illustrate 2-D markers that can be used for a 5 mm instrument shaft and a 5 mm instrument shaft with the markers. FIGS. 17A and 17B respectively illustrate a 2-D markers that can be used for an ultrasound transducer and an ultrasound transducer with the markers. On thinner instruments, multiple rows of patterns can be shifted by a half a pattern to ensure some pattern is fully visible at any angle.

Two-Dimensional Marker Extraction

It is appreciated that a variety of approaches can be used to extract marker features from images and process the extracted information to determine image-derived tool pose estimates. For example, as described below, possible approaches can include a top-down approach, a bottom-up approach, and combined top-down/bottom-up approach.

In a top-down approach, 2-D images can be rendered from a 3-D model of the instrument at a given pose, and the rendered images can be compared with the real input images to evaluate how well they match. The pose that gives the best matching score is the best solution. Although the idea sounds straightforward, in practice it can be difficult to implement due to high related expenses and processing times.

A bottom-up approach tries to find some local feature in the image and then compute the solution. A bottom-up approach can apply to scenarios where salient local features can be extracted and grouped easily, often under some assumptions or using some heuristics. Since local features are more likely to have ambiguity, markers or background color can be added to ensure the robustness of the method. A bottom-up approach is generally more computationally efficient than a top-down approach, since the features can be computed locally and the approach does not involve search or iterative optimization.

A combined top-down/bottom-up approach can be used that integrates the advantages of both of the above two classes of methods. For example, a bottom-up approach can be used to report a finite number of hypotheses, which are then tested and verified using a top-down method. This type of method has sometimes been called "hypothesize and test."

Figure 18:
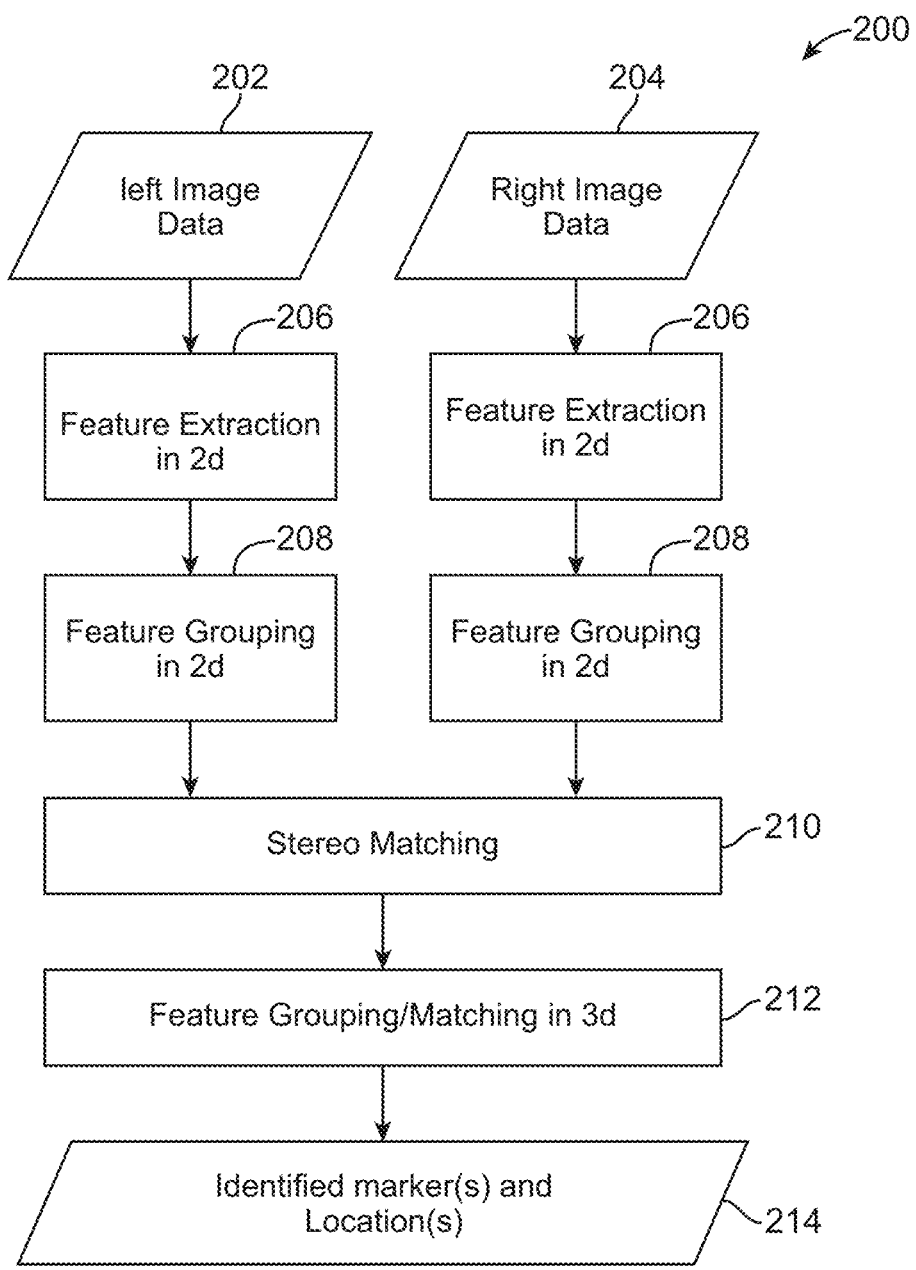
FIG. 18 is a flow diagram of a method for processing stereoscopic images of tool tracking markers, in accordance with embodiments.

FIG. 18 is a flow diagram of a method 200 for processing stereoscopic endoscope images of tool tracking markers. In step 206, left image data 202 and right image data 204 are processed to extract primitive image features. "Primitive image features" refers to visually salient features that can be detected locally, such as blobs and corners. A blob is a small patch With sufficient contrast With respect to its surroundings. A corner is the intersection of two edges. A Maximum Stable Extremal Region (MSER) approach provides an excellent way to detect blobs at an affordable cost. MSER is based on a very minimal assumption of boundary contrast and is therefore able to detect salient regions (blobs) of any size, and any shape. For details on MSER, see J. Matas, O. Chum, M. Urban, and T. Pajdla, "Robust wide baseline stereo from maximally stable extremal regions." In. *Proc.*

BMVC, 2002. We have found MSER to be very effective in detecting artificial fiducial markers.

An alternative feature (blob) detector approach is to use adaptive thresholding plus connected component analysis. The threshold used for binarization is computed adaptively according to the mean grey value of its neighborhood. The kernel convolution to compute the mean at each pixel can be implemented using integral image for fast mean within a rectangular window. A limitation of adaptive thresholding is that it works for a fixed scale. For multiple scales, it has to be run multiple times at different scales. One may also consider to run adaptive thresholding and connected component analysis in a pyramid fashion.

There are many ways to detect corner points from images. For examples of widely used corner detection methods, see Chris Harris and Mike Stephens, "A combined corner and edge detector," pages 147-151, In. *Proc. British Machine Vision Conference,* 1995; and Jiambo Shi and Carlo Tomasi, "Good features to track," pages 593-600, In *Proc. IEEE Conference on Computer Vision and Pattern Recognition,* 1994. For more specific corners (e.g., a saddle point), analysis can be done on the result of the above generic corner detectors to look for the desired properties.

A learning-based approach is also available for dot detection that considers the fine appearance of the dot to disambiguate with background dots (see D. Claus and A. W. Fitzgibbon, "Reliable fiducial detection in natural scenes," In *Proc. European Conf. Computer Vision,* 2004). This approach could be used for more complex marker patterns than dots.

The output from a blob detector is a list of blobs from the image. It can be much faster to analyze these blobs than all the image pixels. We detected the bars of the 2-D markers by checking their flatness (the ratio of the first and second eigen values of the covariance matrix). We detected circles by a simple heuristics that the centroid of a bright blob is inside the bounding box of a dark blob and the bounding box of the dark blob is fully contained by the bounding box of the bright blob. There mart be better ways to detect bars and circles (e.g., by analyzing their higher order moments). Since our overall method is tolerant to the errors in the lower level processing, we have found these methods to be sufficient.

Following the extraction of the primitive image features, the remaining steps of method 200 can be accomplished. In step 208, the extracted features are grouped. Grouping refers to the process of establishing correspondences between the extracted primitive features and the object being imaged, such as a particular marker. This process also needs to account for extracted features that belong to the background instead of the object. The primitive feature grouping relies on knowledge of the marker's configuration to assemble extracted features into groups of features belonging to an), particular marker. In step 210, the grouped features of the left image data 202 are matched with corresponding grouped features of the right image data 204. In step 212, the stereo image matched features can be processed to determine 3-D data for the features. The 3-D data for the features can be processed so as to identify the marker and determine a 3-D pose for the marker (data 214), which can then be used to determine a 3-D pose for the tool having the marker.

Figure 19:
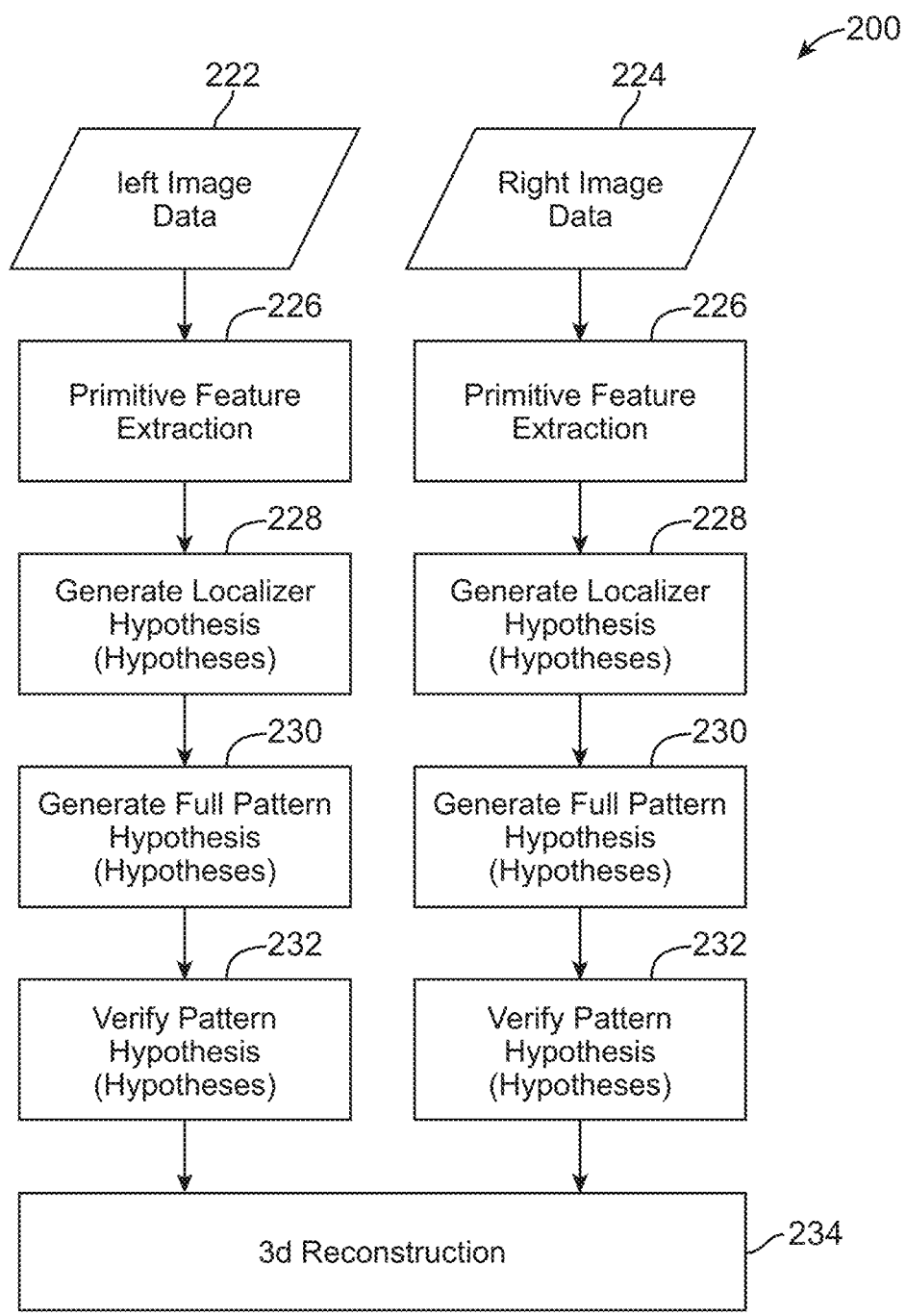
FIG. 19 is a flow diagram of a method for processing stereoscopic images of 2-D tool tracking markers, in accordance with embodiments.

FIG. 19 is a flow-diagram of a method 220 that can be used for processing stereo images of tool tracking markers (embodiments of which are shown in FIGS. 13A and 13B). Method 220 follows a "hypothesize and test" framework. In step 226, the left image data 222 and the right image data 224 can be processed to extract primitive features, which can be accomplished using a variety of methods such as an above described method.

In step 228 some of the extracted primitive features are processed so as to generate one or more localizer hypotheses (for one or more markers) by identifying one or more primitive features that exhibit characteristics of one or more marker localizer features. A localizer hypothesis is a tentative assumption that one or more extracted primitive features correspond to one or more localizer features in a marker. One or more localizer features can be used to determine positional and at least partial orientation of the marker. For example, in the 2-D markers of FIGS. 13A and 13B, the four circles and the bar can be used as localizer features. With these 2-D markers, the extracted primitive features (or the image data in general) can be processed to look for two circles (designated in FIGS. 13A and 13B as "0" and "1") within a minimum and maximum distance that have a bar in the middle that is aligned With a line connecting the two circles. By identifying the side of the line that the bar is on, a partial orientation of the pattern can be determined (i.e., about a line in the image). It is appreciated that a range of different marker patterns can be used and that various combinations of any of the features within a marker pattern can be used as one or more localizer feature.

In step 230 the extracted primitive features are processed so as to generate one or more full pattern hypotheses. A full pattern hypothesis is a tentative assumption that multiple primitive features correspond to one or more marker features that can be used to determine the basic position and orientation of the marker pattern within the image, which can be skewed or foreshortened as determined by the 3-D pose of the marker relative to the imaging device. For example, with the 2-D marker patterns of FIGS. 13A and 13B, the localizer hypothesis (the identified circles "0" and "1" with the bar in between) can be used as a starting point to search for the remaining localizer circles (designated in FIGS. 13A and 13B as "2" and "3"). The search can look for all the compatible localizer "2" and "3" features within a search area defined by a minimum and a maximum pattern skew, and a minimum and a maximum pattern aspect ratio. Advantageously, the "2" and "3" circles do not have bar between them, which can be used to aid in their identification. The combination of the localizer hypothesis and the identified "2" and "3" localizer circles can be used generate a full pattern hypothesis. The full pattern hypothesis can also be checked to see if its perspective is less than a maximum value, by which the consistency of skew and aspect ratio can be checked.

In step 232 one or more of the generated full pattern hypotheses are verified by processing the image features so as to identify the marker. It is appreciated that a varietv of approaches can be used to process the image data so as to identify the marker. For example, in method 220 the generation of a full pattern hypothesis provides information regarding the position and orientation of a marker pattern within the image. This information can be used to orient or align candidate marker patterns with the imaged pattern. The imaged patterns and the aligned candidate marker patterns can then be checked for consistency. Where consistency exists, the imaged marker pattern can be identified as the candidate marker pattern. For example, with the 2-D marker patterns of FIGS. 13A and 13B, the location of detected 2-D blobs within a full pattern hypothesis can be compared with locations of information bits set to "1" (i.e., physically present) of a candidate marker pattern model that has been aligned with the full pattern hypothesis.

The alignment of a candidate marker pattern with a marker image can be accomplished by estimating the 3-D pose of the marker relative to the imaging device and aligning a candidate marker with the estimated pose. Pose estimation computes the 3-D pose of the marker by knowledge of the 3-D geometry of the marker and its 2-D projections in the image. The imaging-device calibration is used in the pose estimation process using known methods. For the two dimensional marker patterns of FIGS. 13A and 13B, the pose estimation can be accomplished using the locations within the image of the four localizer circles. Once the pose of the marker relative to the imaging device is estimated, the 3-D coordinates of a candidate marker's features can be determined and be projected into the image using the known image-device calibration. The pixels at these image locations can be checked to decide if there is a dot at that location.

The alignment of a candidate marker pattern with a marker image can also be accomplished by homography. Four 2-D point correspondences define a plane perspective transformation (i.e., homography), which contains all the possible transformations of a plane under perspective transformation. Even though a marker pattern attached to a cylindrical tool shaft is not planar, a plane approximation can be useful for a wide range of viewpoints. This approach involves an approximation that the marker features reside on a plane, which provides a simplified process for aligning a candidate marker pattern with a marker image. For example, the image locations for the dots can be based on the image locations of the four circles by assuming the pattern is attached to a plane through a plane perspective transformation (see R. Hartley and A Zisserman, "Multiple View Geometry in Computer Vision," chapter 2, Cambridge University, Press, 2000). Due to the deviation from the planar assumption, the "planar" model dots do not exactly coincide with the marker image dots. To compensate for the planar assumption, the on/off status of a model dot can be determined using a nearest-neighbor scheme. When the nearest-neighbor scheme fails, the verification fails. Empirically, homography has been found to be able to detect the 2-D pattern correctly for oblique angles up to 45 degrees. Compared to pose estimation, alignment by homography is an approximation. However, it is still appealing in that the imaging-device calibration is not required. Additionally, the exact 3-D geometry of the marker does not need to be known (e.g., it does not matter if the marker is attached to a 5 mm, a 8 mm, or a 10 mm tool shaft) and therefore allows markers to be attached to different instrument geometries at the same time. These flexibilities may not be critical in a surgical instrument tracking application but may enable other applications.

Marker design is closely related to how marker features are detected from images. The design of marker embodiments disclosed herein and feature detection methods disclosed herein have been co-evolved for better overall system performance. For example, with respect to the 2-D marker patterns of FIGS. 13A and 13B, if the bar between the localizer circles "0" and "1" did not exist, the specific details of the detection method would likely need to be modified. However, it is appreciated that a wide variety of marker patterns and corresponding marker feature detection methods can be practice and still be within the spirit and scope of the present invention.

Figure 20A:
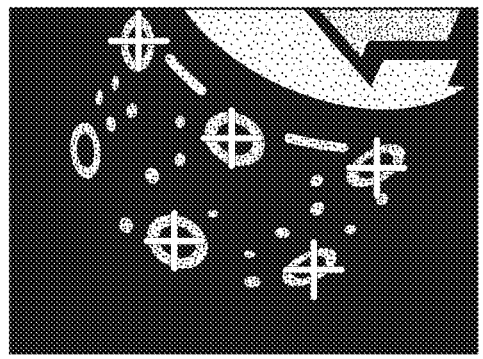
FIGS. 20A through 20E illustrate steps for processing an image of a 2-D tool tracking marker, in accordance with embodiments.
Figure 20B:
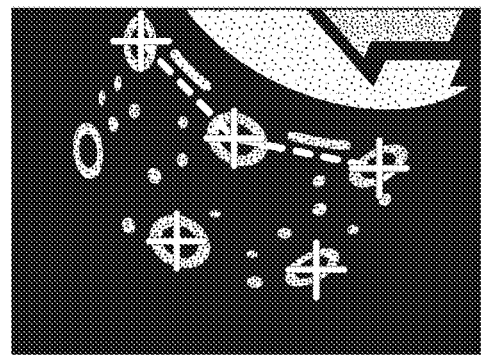
Figure 20C:
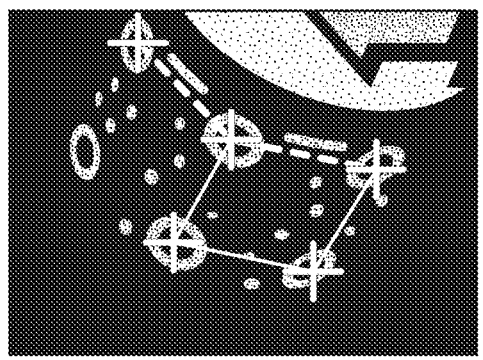
Figure 20D:
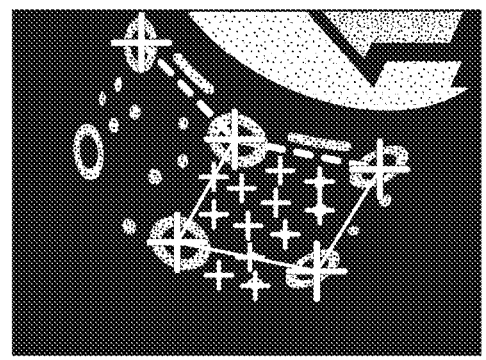
Figure 20E:
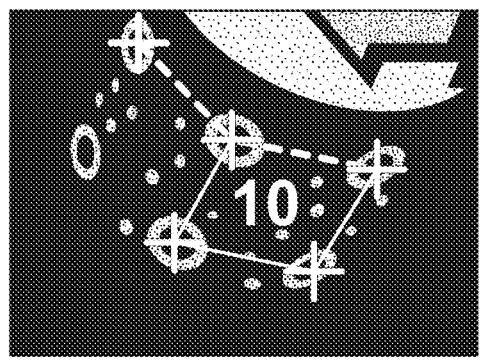

FIGS. 20A, 20B, 20C, 20D, and 20E illustrate the method of FIG. 19 as applied to the 2-D marker of FIG. 13B. In FIG. 20A, the bright circles in the image are detected (as shown by the cross-hair annotations). In FIG. 20B, two localizer hypotheses are formed using adjacent bright circles that have aligned bars. In FIG. 20C, a full pattern hypothesis is formed by identifying the designated bright circles by searching relative to the associated localizer hypothesis. In FIG. 20D, a candidate marker pattern is aligned with the image full pattern hypothesis and the location of candidate marker pattern features relative to the image are determined. The determined locations are used to check the image to see if corresponding detected features are present. When the patterns match, a candidate marker pattern is verified (FIG. 20E illustrates an exemplary pattern identification code for a verified candidate marker pattern). It is appreciated that any existing pose estimates, such as a raw kinematics pose estimate or a corrected kinematics pose estimate, may be used to limit the number of candidate marker patterns. It is also appreciated that the detected marker features may be used directly to determine an identification of a marker pattern by determining directly what marker pattern features are present and which are not present.

Figure 21A:
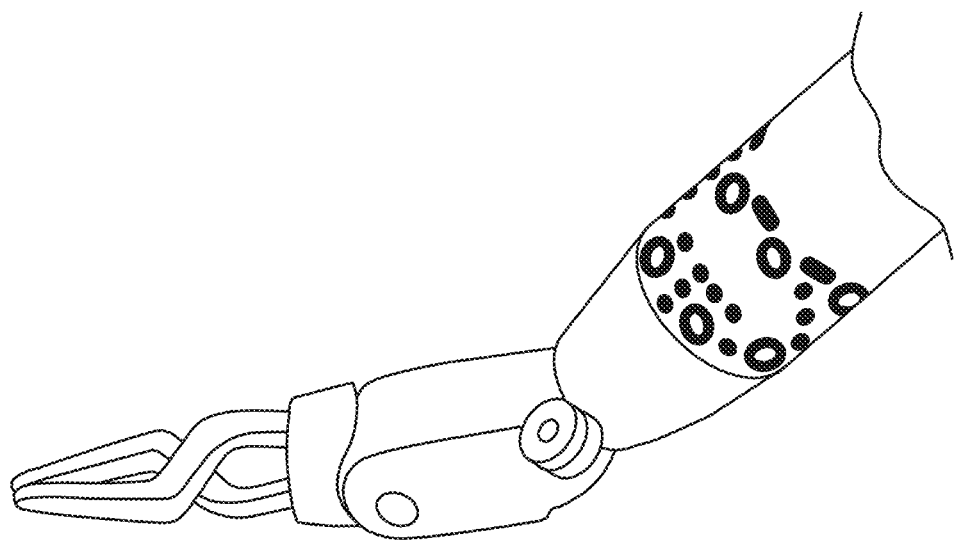
FIGS. 21A and 21B illustrate how markers at multiple locations can support different operational ranges, in accordance with embodiments.
Figure 21B:
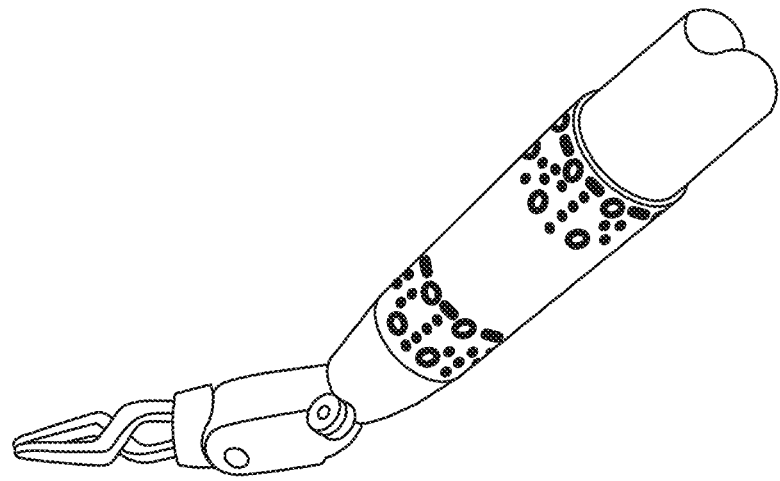

Marker patterns can be arranged on a tool in a variety of ways for a variety of purposes. For example, markers can be arranged at multiple locations on a tool so as to provide for multiple operational ranges. FIGS. 21A and 21B illustrate a robotic surgical tool having two circumferential bands of markers that are separated by an axial distance along the tool shaft. In FIG. 21A, the tool is being operated close to the imaging device, thereby placing one of the bands of markers outside the view. In FIG. 21B, the tool is being operated farther away from the imaging device, thereby placing both bands of markers within the view. As shown in FIG. 21B, the features in the marker-band closest to the imaging device are larger than the features in the marker band farthest from the imaging device. These larger features may be more readily detectable as compared to the smaller, farther away features, especially if the marker features farthest away are partially or fully occluded, such as by patient tissues or fluids. As shown in FIG. 21A, the band of markers disposed closest to the distal operating end of the surgical tool can provide distinct features for imaging when the other band is out of view.

One-Dimensional Marker Designs

Figure 22A:
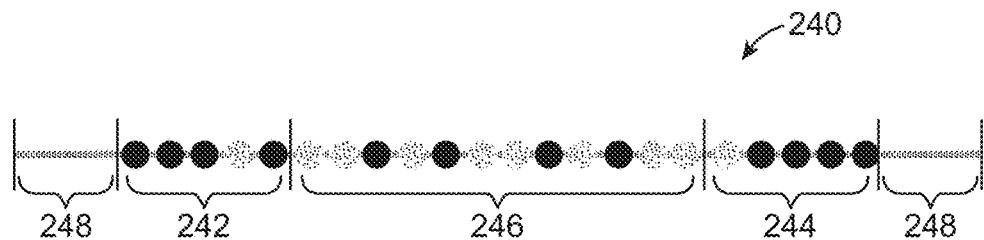
FIG. 22A diagrammatically illustrates a one-dimensional (1-D) tool tracking marker, in accordance with embodiments.
Figure 22B:
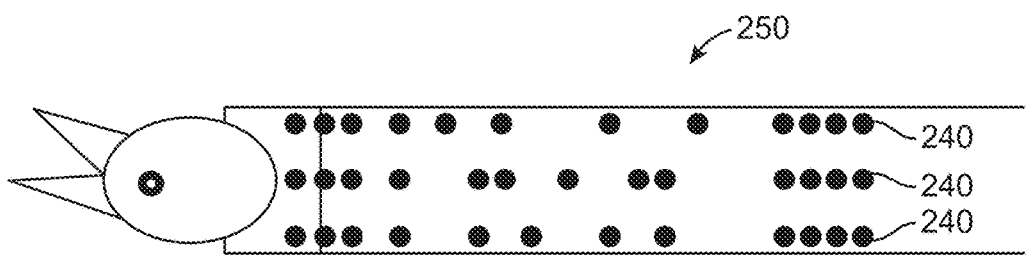
FIG. 22B diagrammatically illustrates a surgical tool having multiple 1-D tool tracking markers, in accordance with embodiments.
Figure 22C:
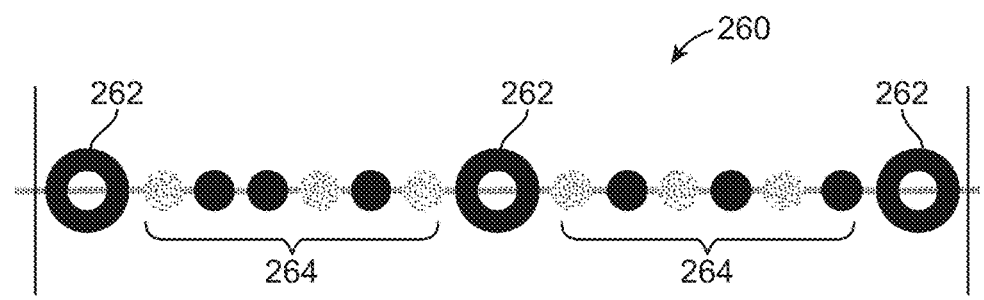
FIGS. 22C and 22D diagrammatically illustrate another 1-D tool tracking marker, in accordance with embodiments.

One-dimensional markers can be used to determine instrument pose. A 1-D marker includes primitive features arranged in one dimension. Some of the features can serve as localizer features, and the rest of the features can serve as identification features. Similar to 2-D markers, localizer features can be used to provide positional or orientation information to determine the pose/alignment of the marker, and identification features can be used to differentiate different markers. Identification features can follow a coding scheme and can include redundant information for error checking and/or correction. For example, FIGS. 22A, 22B, and 22C illustrate 1-D markers, which employ dots, or a combination of circles and dots. FIG. 22A illustrates a 1-D marker 240 that includes dots forming a straight line. While it is appreciated that different colors can be used to convey information, marker 240 employs dots that are either present (i.e., set to "1") or absent (i.e., set to "0"). Marker 240 includes a start pattern 242, an end pattern 244, and a center portion 246 having 12 data bits. These 12 data bits can be used in a variety of ways, such as by using some of the data bits as identification bits and some of the data bits as error checking/correction bits, which can include one or more checksum data bits. The start pattern 242 and the end pattern 244 can be delineated by adjacent blank areas 248.

One-dimensional patterns have advantages and disadvantages. For example, an advantage of using a 1-D pattern is that it works for very thin instruments, such as a needle where a 2-D pattern would not work. A disadvantage of a 1-D pattern is that a single 1-D marker does not give the full six-dimensional pose for the object. At least two non-collinear markers are required for a full six-dimensional pose. For very thin objects, the axial roll is not typically observable, so the five-dimensional pose provided by a single 1-D marker is already the most that can be typically obtained.

FIG. 22B illustrates an image of a surgical tool 250 having 1-D markers 240, shorting three such markers 240 placed in alignment with the surgical tool's shaft axis. When attaching a 1-D marker to a cylindrical surface, the marker can be aligned with the axis of the cylinder, which results in the marker being disposed along a straight line in 3-D space. Such markers may be particularly advantageous when used on relatively small diameter tool shafts, where more 1-D markers can typically be arranged around the shaft than comparable 2-D markers. However, one concern with a 1-D marker is the length that it requires on an instrument shaft, which may, become an issue at close operational ranges that may result in part of a 1-D marker being out of view.

FIG. 22C illustrates a modified version of the 1-D marker 240 of FIG. 22A. Marker 260 incorporates circular features 262 that can be used as localizer features similar to the localizer features of the 2-D markers of FIGS. 13A and 13B described above. Advantageously, the use of the circle features 262 may help to reduce the length of the pattern, thereby providing a better close range pattern. Dots 264 can be used for marker identification and error checking/correction data.

Figure 22D:
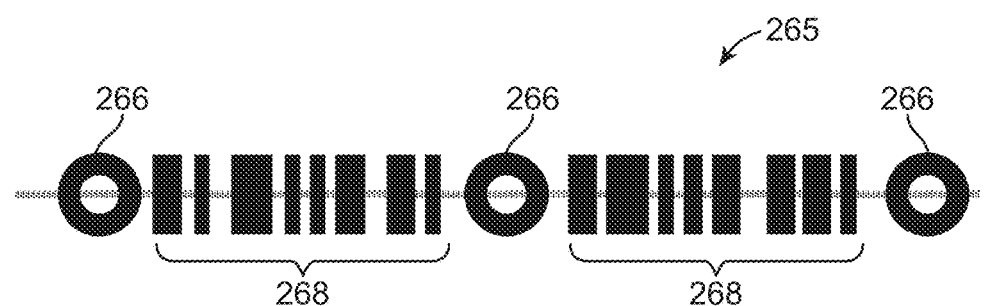

FIG. 22D illustrates an alternative version of the 1-D marker 260 of FIG. 22C. Marker 265 incorporates a combination of circular features 266 and bar features 268. Circular features 266 can be used as localizer features and bar features 268 can be used for marker identification and error checking/correction data. A difference between dots 264 of marker 260 and bar features 268 of marker 265 is that with marker 265 information is coded by the positions of the transitions between dark and bright regions, whereas marker 260 uses the positions of the centers of the dots to carry information.

One-Dimensional Marker Extraction

Figure 23:
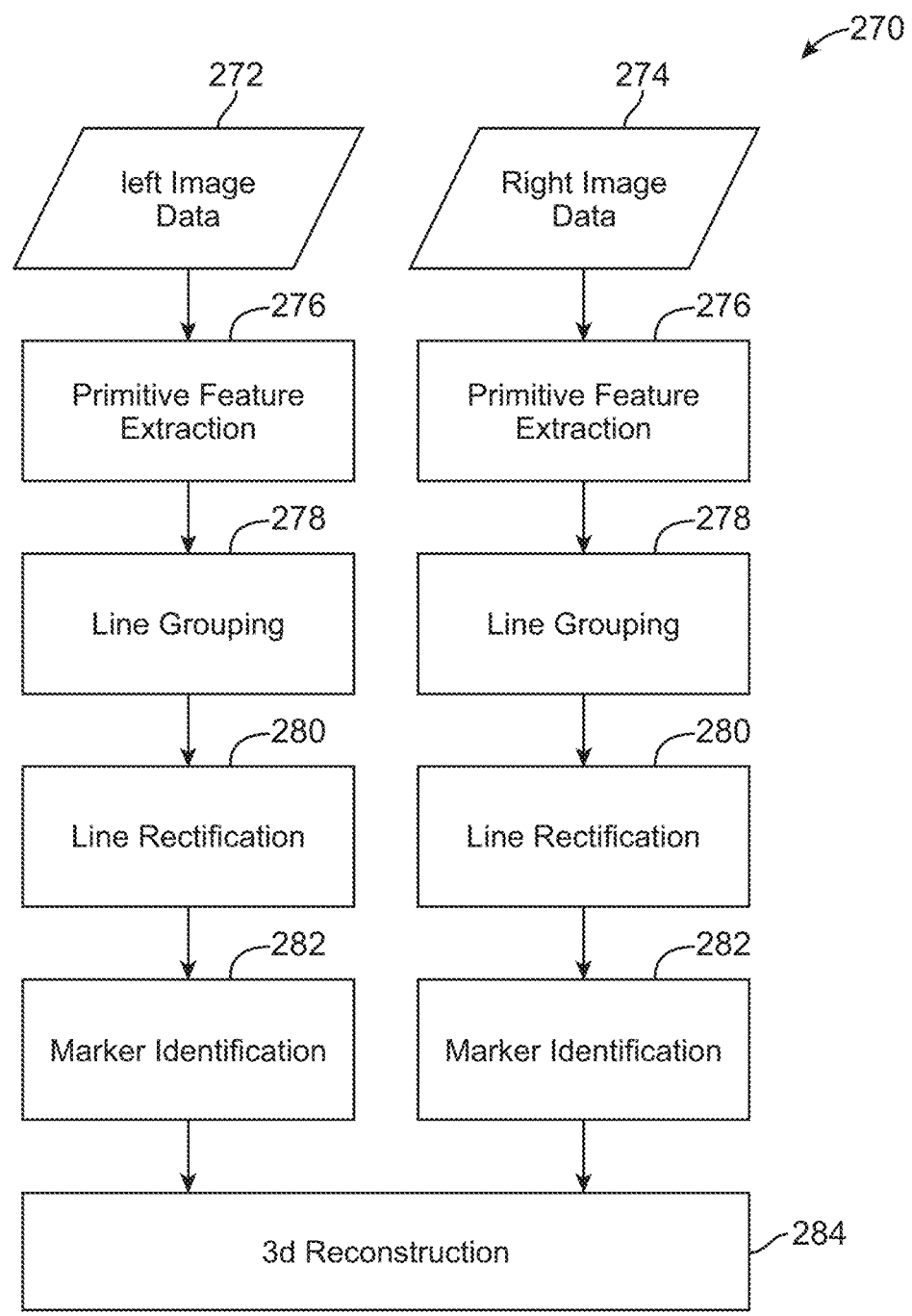
FIG. 23 is a flow diagram for processing stereoscopic images of 1-D tool tracking markers, in accordance With embodiments.

FIG. 23 is a flow diagram of a method 270 that can be used for processing stereo images of one or more 1-D tool tracking markers (embodiments of which are shown in FIGS. 22A, 22B, and 22C). In step 276, left image data 272 and right image data 274 can be processed to extract 2-D blobs (i.e., features), which can be accomplished using approaches as described above with reference to the extraction of 2-D blobs from 2-D markers (see FIG. 19 and related discussion). In step 278, the extracted blobs are grouped into lines. Line grouping can be performed using a Random Sample Consensus (RANSAC) approach by extracting multiple straight lines from all the detected feature points. (For details of Random Sample Consensus, refer to M. A. Fischler and R. C. Bolles, "Random sample Consensus: A paradigm for model fitting with applications to image analysis and automated cartography" *Comm. of the ACM,* 24: 381-395, 1981, which is hereby incorporated by reference.) More discriminative features against background clutter, such as the circles in the marker of FIG. 22C, can also be used to form hypotheses.

In step 280, one or more lines are rectified. Line rectification refers to removing the perspective effect on the line to restore the metric relationship of the information bits (e.g., dots). The vanishing point of the lines parallel to the shaft is sufficient to rectify the line. (See R. Hartley and A Zisserman, "Multiple View Geometry in Computer Vision," Cambridge University Press, 2000, which is hereby incorporated by reference.) There are a number of ways to obtain the location of the vanishing point. For example, if there are more than one visible linear markers on the shaft, the vanishing point is the intersection of these lines. As another example, images of points with equal or known spaces can be used to compute the vanishing point. (See, for example, FIG. 22C for examples of linear markers having equally spaced circles.)

In step 282, one or more markers are identified. Marker identification can involve locating the start and end patterns and then reading the data bits to identify the pattern. It is appreciated that the coding scheme can be designed so as to encode sufficient redundancy for error checking. Where some data bits have been used for error checking, the error checking bits can be read to validate the identification. As discussed above, the error checking data bits can include at least one data bit used as checksum data.

When a stereo camera is used, once a marker (1-D or 2-D) has been identified, the 3-D reconstruction of step 282 becomes a simple step. The correspondences between the imaged features in both the left and right images are known at this state, and only triangulation is needed. The resulting 3-D marker feature locations can then be used in combination with the known relative spatial arrangement of the marker features relative to the tool to determine a 3-D pose for the tool.

Configuration Marker

A tool, such as the surgical tool 26, can be configured to include a configuration marker so as to provide multiple primitive features that can be detected within an image. An individual primitive feature is usually not sufficient to serve as a marker because it may not be unique and does not provide enough geometric constraints to determine object pose. A number of primitive features can be used to form a pattern having a unique configuration in 3-D space, which is herein referred to as a "configuration marker." The pattern (i.e., configuration) as a whole combines the discriminative power of each individual primitive feature and that of their geometric relationship to be more easily detected from the background. Three non-collinear features extracted from stereo images provides sufficient information to determine pose for the tool. However, having more features than the minimum requirement can be beneficial in gaining more confidence in detection and better accuracy in pose determination. The shape or appearance of the primitive features can be identical (e.g., circular disks of the same size), can include a few variations, or can be unique. As such, a wide variety of primitive features can be used, such as circles, dots, bars, corners, etc. Where the primitive features used include some level of variations, the resulting differences in appearance can be used to help match image locations for particular features between two stereoscopic images (i.e., using feature signatures during feature matching) and the images with the model (i.e., using feature signatures invariant or less sensitive to viewpoint and lighting changes).

One such primitive feature is a reflective spherical surface. A reflective spherical surface has the nice property that it appears as a bright spot irrespective of viewpoint as long as a light source and an imaging device are aligned along a common direction, as is tropically the case with endoscopic imaging during minimally-invasive robotic surgery. The center of the bright spot also coincides with the projection of the center of the spherical surface. A reflective spherical surface can be either concave or convex. In most cases, a reflective spherical surface may produce a bright spot with sufficient contrast with respect to its background to allow detection in an image for a variety of viewpoints and distances. However, this contrast may be reduced to an undesirable level if the adjacent background surfaces are perpendicular to the light direction and the entire area reflects a significant amount of light back at the imaging device (thereby leading to image saturation). In this circumstance, improved gain control or a high dynamic range video may help alleviate the problem.

Figure 24:
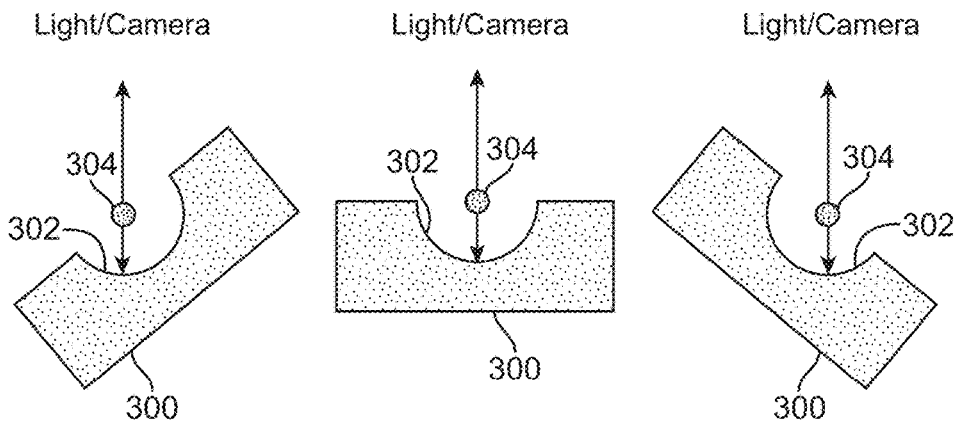
FIG. 24 diagrammatically illustrates primitive features, each feature having a reflective concave spherical surface, being illuminated/imaged from three different directions, in accordance with embodiments.

FIG. 24 illustrates a primitive feature 300 that includes a concave spherical surface and that is being illuminated/imaged from three directions. The spherical surface 302 of the marker 300 has a center point 304 through which illumination light that is reflected directly back towards the imaging device travels. Illumination light that does not travel substantially through the center point is reflected away from the illumination/imaging direction.

Some natural features on a tool (or mechanical device in general) may also appear as salient visual features in captured images. These natural features may provide additional image-derived information regarding the 3-D pose of a tool. Examples of such natural features for an exemplary surgical tool can include the end of a bolt having an approximately spherical surface, and the end of a hinge of an articulated instrument having a reflective concave spherical surface. Such natural features may form stable bright blobs in images similar to those of artificial markers. However, for many tools, such natural features by themselves may not provide a sufficient number of features to form patterns distinctive enough to be extracted against a cluttered background. By introducing artificial primitive features in conjunction with such natural features, sufficient distinctiveness can be achieved. The use of existing natural features helps reduce the number of artificial features added and therefore reduces the changes (such as appearance) to the mechanical device to be tracked.

Figure 25:
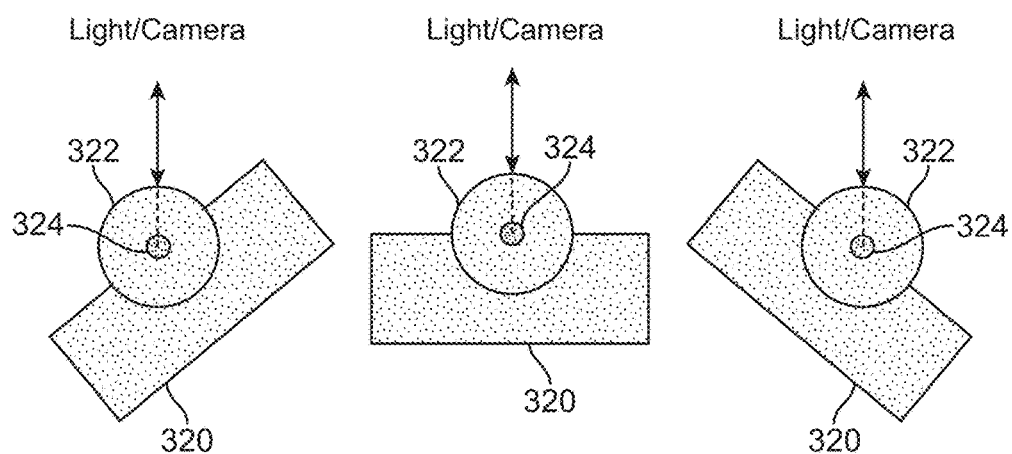
FIG. 25 diagrammatically illustrates primitive features, each feature having a reflective convex spherical surface, in accordance with embodiments.

FIG. 25 illustrates a primitive feature 320 that includes a convex spherical surface 322 and that is being illuminated/imaged from three directions. Similar to the primitive feature of FIG. 24, the spherical surface 322 has a center point 324 through which illumination light that is reflected directly back towards the imaging device travels. Illumination light that does not travel substantially through the center point is reflected away from the illumination/imaging direction. Reflective convex spherical surfaces may be more suitable for surgical applications than concave reflective spherical surfaces in that blood (or any fluid or substance in general) may be more easily trapped in concave recesses, which may cause a concave primitive feature to lose its contrast with adjacent areas of the tool, or become darker than adjacent areas depending on the amount of blood trapped. In contrast, a reflective convex spherical surface is less likely to trap blood. Furthermore, the interaction of the reflective convex spherical surface and tissue ma, help keep the surface clean, which may help it to produce a bright spot even in a heady blood field.

Figure 26A:
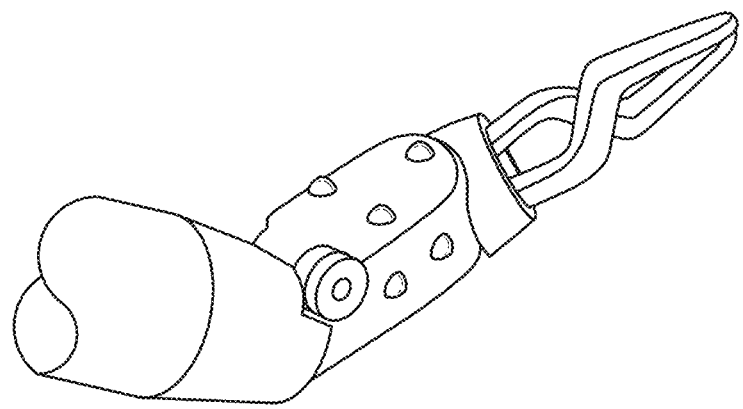
FIGS. 26A and 26B are endoscopic images of prototype surgical tools having point configuration markers With reflective spherical surfaces, in accordance with embodiments.
Figure 26B:
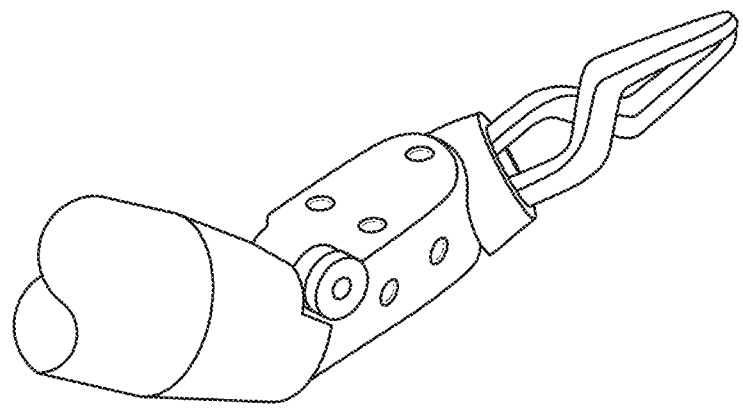

FIGS. 26A and 26B show surgical tools having primitive features with reflective spherical surfaces. These surgical tools are for use without any special illumination, but instead are for use with an existing stereo imaging system used by a surgeon to view a procedure site in an exemplar, robotic surgery system. This use is in contrast with existing systems that use controlled active infra-red (IR) illumination, which ensures that only the marker points are bright in the view, which significantly simplifies related image processing and estimation. However, the use of an existing stereo imaging system avoids the added system complexity associated with controlled active IR illumination. Although these surgical tools may have primitive features placed on their distal clevis, it is appreciated that primitive features can be placed at other locations, such as on the instrument shaft and/or the proximal clevis. It may be advantageous to select locations that are not prone to reflective image saturation.

Configuration Marker Detection

Figure 27:
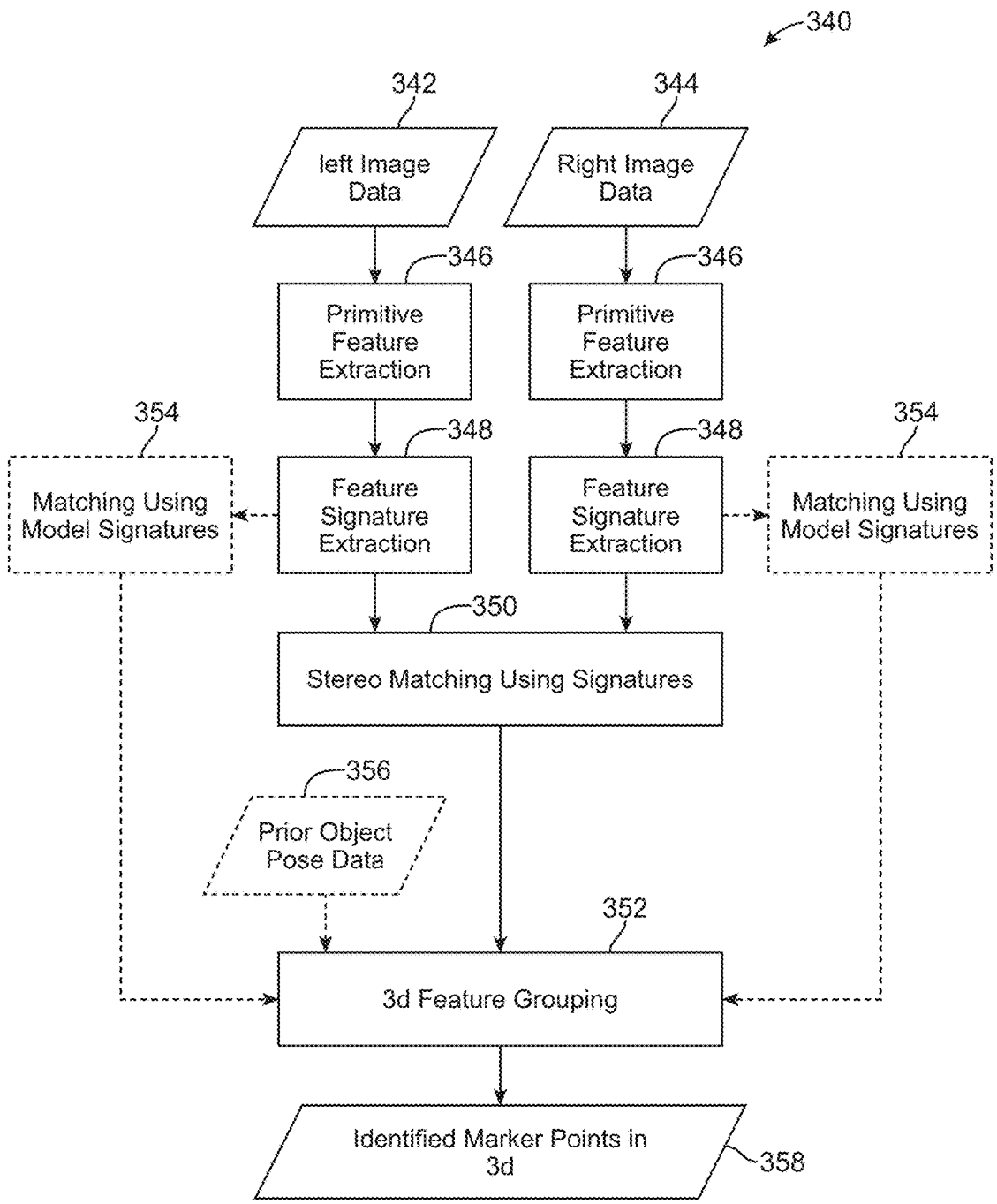
FIG. 27 is a flow diagram of a tool tracking method that employs processing of stereoscopic images of a surgical tool having primitive features with reflective spherical surfaces, in accordance with embodiments.

FIG. 27 is a flow diagram of a tool tracking method 340 that employs processing of stereo images of a tool having a configuration marker. The method makes use of the geometric invariance between the primitive features in 3-D space, therefore stereo matching/3-D reconstruction is performed first. In step 346, left image data 342 and right image data 344 can be separately processed so as to extract primitive features that exhibit a qualifying amount of contrast relative to adjacent areas (i.e., bright spots).

In step 348, the extracted primitive image features are processed so as to identify "image signatures" that are consistent with the primitive features used. "Signatures" can be extracted for every primitive image feature. Where the primitive features used are identical in shape, their image signatures may be substantially similar. Where the primitive features used have shape or appearance variations, the resulting differences in appearance can be used to help associate a particular primitive feature with a particular primitive image feature, such as a bright spot. A primitive image feature signature can be extracted from the primitive image feature (i.e., image patch) around the feature point. A simple feature signature approach is to use the extracted primitive image feature (image patch) itself as used in traditional stereo. More recently, signatures that are invariant/insensitive to some transformation or deformation have been proposed that are capable of handling more illumination and viewpoint change than image patch. Histogram of Gradient (HOG) is a good example. (See D. Lowe, "Distinctive image features from scale-invariant keypoints," In. *International Journal of Computer Vision*. volume 20, pages 91-110, 2003, which is hereby incorporated by reference.)

In step 350, features in the two stereo images (e.g., left image and right image) are matched. Different signatures approaches may require different matching methods. For example, normalized correlation is used for an image patch signature (see David Forsyth and Jean Ponce, "Computer Vision A Modem Approach," page 240, Prentice Hall, 2003). With an HOG signature, it has been proposed to use the relative matching score as a measure of confidence, which may likely be a useful approach. Epipolar constraint can be used to constrain the matching only on a straight line (see R. Hartley and A. Zisserman, "Multiple View Geometry in Computer Vision," Cambridge University Press, 2000). Where multiple good matches exist, all can be kept for processing in the next step. The matched features are used to generate 3-D coordinates by using stereo triangulation.

In an optional approach to step 350, model based signatures may be used in step 354. Matching feature signatures between image and model is expected to be more difficult than matching feature signatures between left and right stereo images since stereo images have similar viewpoints, illumination, and epipolar constraint. In order to match image signatures with model signatures, the features may need to be invariant to viewpoint and lighting conditions. If identical primitive features are used, it may be more difficult to match against a model. However, primitive features can be designed to have shapes (and resulting appearances) that are eases to match under large viewpoint variations. One approach is to rely on topological properties that are invariant to viewpoint change. An example is a circle, such as described above with reference to 1- and 2-D markers. As a variation on a circle, a primitive feature can use multiple bright dots inside a dark dot. Even if not all of the dots are matched with a model, or even if the matches are not unique, partial matching can be useful in feature grouping.

In step 352, the matched features are used to perform 3-D feature grouping so that the correspondence of the observed features with features in the model is established (i.e., to get identified marker points in 3-D 358). The process uses 3-D positions of the features and optionally their matching score with the model primitive features and/or optionally prior knowledge on the instrument pose. Step 352 can be performed by a "Constellation algorithm." The Constellation algorithm performed is an efficient Bayesian approach for 3-D grouping based on geometric constraint, appearance constraint, and other prior pose information on the object pose (i.e., prior object pose data 356). The use of appearance constraint is an option if the geometric constraint is insufficient. The output of the Constellation algorithm is the label for each observed feature, taking values from one of the model primitive features or background clutter. Random Sample Consensus (RANSAC) is used at the end to enforce the rigidity constraint.

The Constellation Algorithm—Problem Formation

Assume we have n known patterns $\{C_1, \ldots C_n\}$, each of which contains $k_i$ nodes. We use $C_o(k_o=1)$ to denote anything which is not part of the pattern.

$$\sum_{i=0}^{n} k_i = t.$$

Assume the nodes are contiguously labeled as $0, \ldots, t$. We use p[i] to refer to the index of the pattern of a node label i. $c_1, \ldots, c_t$ are the coordinates of the nodes in some coordinate system (it is OK that each pattern has its own coordinate system). There are m input nodes with label $1, \ldots, m$ and coordinates $p_1, \ldots, p_m$. The input nodes contains an unknown number of patterns. Missing data and background nodes can exist. We denote $O=[o_1, \ldots, o_m]$ to be the ownership of each input node: $o_i \in [0, t]$. It is possible that we know a priori knowledge of the ownership of each input node. The prior ownership knowledge can be from local node observation (independent of other nodes) or other sources. $q_i(1)$ denotes the probability of input node i corresponds to model label l. $q_i(0)$ should be set to be a small probability.

Each input node can take t labels, therefore the total number of possible solutions is $m^t$. Solving it by trying every possibility is an exponential problem. If the prior ownership knowledge is strong, this problem can be solved by a randomized "hypothesize and test" approach (i.e., RANSAC). However if there is no or weak prior ownership knowledge, the generated hypotheses are almost random and the performance is close to an exhaustive search.

Here we simplify the problem by considering pair-wise distance constraints. We add a link between any two input nodes whose distance is less than the maximum distance between two model nodes plus allowed error. This results in a graph. The joint probability of the graph is therefore defined by pair-wise distance compatibilities and the prior ownership knowledge probabilities.

$$P(O) = \frac{1}{Z} \left( \prod_{i,j \in [1,m], \|P_i - P_j\| < \epsilon} \psi(o_i, o_j) \right) \left( \prod_{i \in [1,m]} q_i(o_i) \right) \quad (1)$$

where $\psi_{i,j}(o_i, o_j)$ is the pair-wise distance compatibility function within each pattern. $\epsilon$ is a neighborhood radius defined by the maximum pattern spread in the model.

$$\psi_{i,j}(o_i, o_j) = \quad (2)$$

$$\begin{cases} \frac{1}{\sigma\sqrt{2\pi}} \exp\left\{-\frac{(\|c_{o_i} - c_{o_j}\| - \|p_i - p_j\|)^2}{2 * \sigma^2}\right\}, & \text{if } p[o_i] = p[o_j] \text{ and } o_i \neq o_j; \\ 0 & \text{if } o_i = o_j \text{ and } o_i > 0 \\ \alpha & \text{otherwise} \end{cases}$$

where $\sigma$ is the measurement noise of the distance between nodes and $\alpha$ is a background likelihood Which should be lower than the likelihood of a true match.

The prior knowledge on the pose of the object can be used as the following. The prior on translation can be represented in the prior q( ) since this knowledge can be applied to each individual node. The prior on rotation can be represented in the pair-wise potential $\psi( )$ by the relative orientation of two nodes.

The Constellation Algorithm—A Belief Propagation Solution

The joint probability function, equation (1), is in a form of a combination of local potentials and pair-wise potentials. This problem can be solved efficiently using the belief propagation (BP) algorithm. The algorithm gives the marginal distribution (ownership) of each node as output. In these particular cases, the interconnection of the nodes can form loops. This class of method is referred to as loopy belief propagation (see K. Murphy, Y. Weiss, and M. Jordan, "Loopy-belief propagation for approximate inference: An empirical study," In *UAI*, volume 15, pages 467-475, 1999). It shows very good empirical result even though the optimality is not proven. For details on the implementation of the BP algorithm, see Judea Pearl, "Probabilistic Reasoning in Intelligent Systems: Networks of Plausible Inference," Morgan Kaufmann, 1988.

The Constellation Algorithm—Verification

It is possible that some of the nodes get incorrect labels in the solution from BP because it only enforces local constraints. However it is expected that a large part of the nodes can get correct labels. This is a big advantage compared to a random guess of the label. A verification step should follow to enforce the global rigidity constraint. This step can be achieved using RANSAC on the correspondences from BP.

Discernible Markers

Figure 28A:
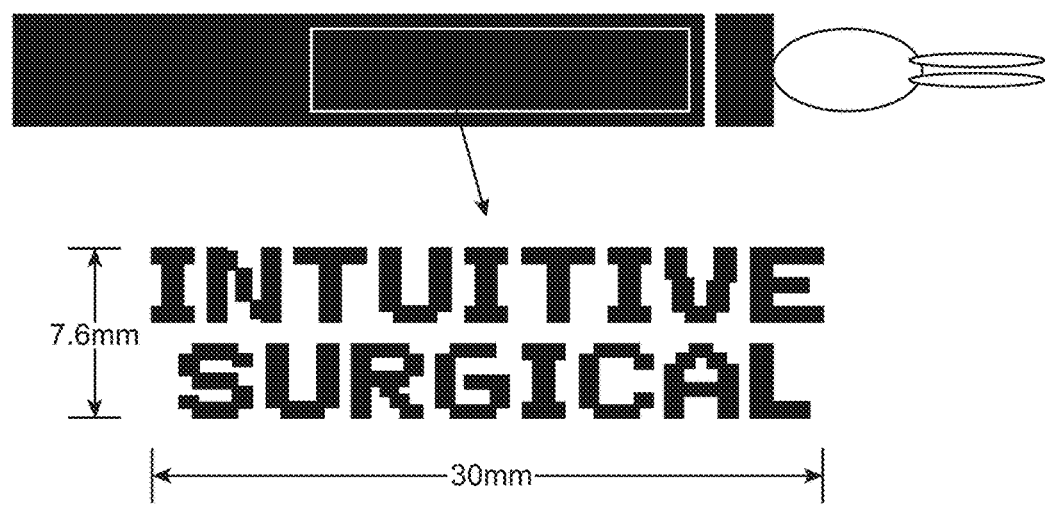
FIGS. 28A and 28B illustrate discernible tool markers, in accordance with embodiments.
Figure 28B:
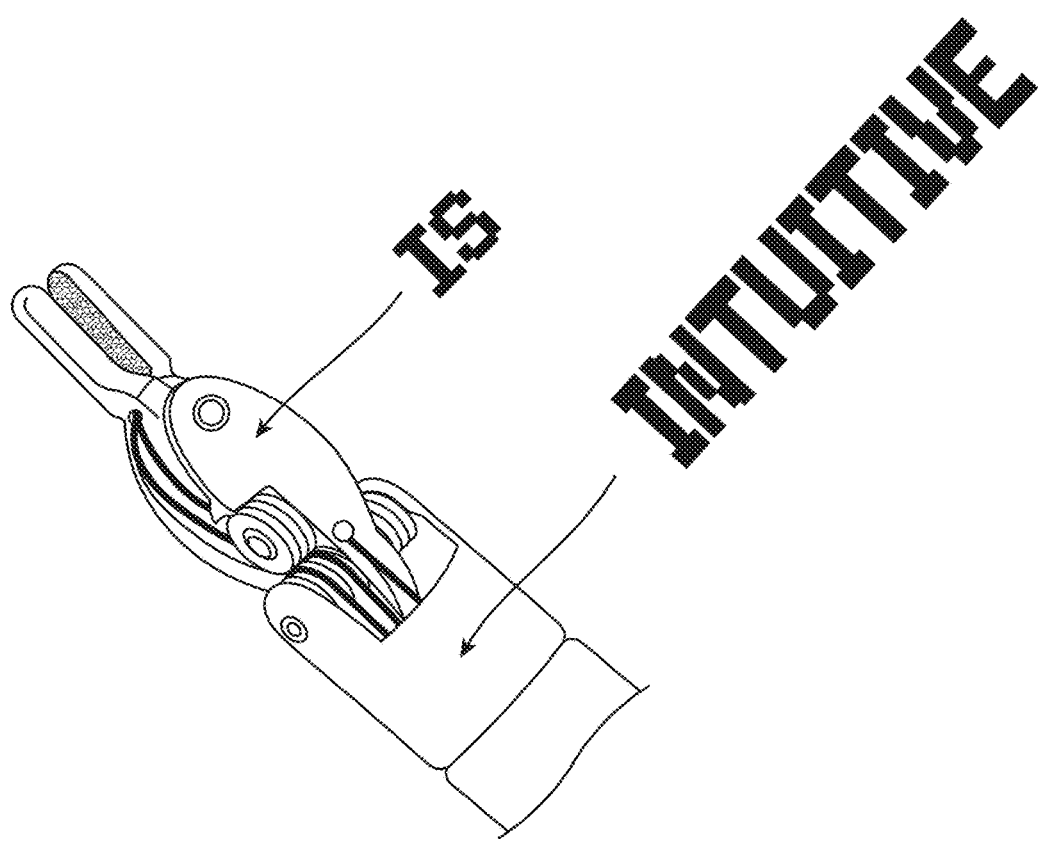

A discernible marker that includes text and/or one or more symbols can be used for tool tracking. Such a discernible marker can include a wide range of text and symbols. For example, a discernible marker can include a company name, a company trademark symbol, a product name, a product trademark symbol, a component name, and/or a user name. A discernible marker can use a variety of colors set on a variety of backgrounds. For example, text and/or symbols may be light colored (such as white) set against a dark background (such as black), and vice-versa. FIGS. 28A and 28B illustrate some exemplary discernible tool markers. It can be advantageous to use a discernible marker that is familiar to a human user. Familiar information tends to blend well with the scene and may cause less distraction to users compared to other markers with similar information content.

Discernible markers can include local features that can be used for object pose estimation. Standard text can be used as markers. However, some modifications to the font can increase the number of stable features (e.g., corner points), create features that are highly discriminative against background (e.g., a corner within a "checkerboard" pattern or array, or a saddle point), and/or enable more efficient detection methods. For example, a marker can include text and/or a symbol that is constructed from a number of rectangular elements selected from a rectangular "checkerboard" array. The selected elements can have a color or a range of colors, and the unselected elements can have a contrasting color or range of colors. Local patterns of the selected and/or unselected elements can provide a local feature that can be imaged and processed so as to determine position and/or identification information for the local feature. Such local patterns can include a variety of patterns. For example, a local pattern can include variations in the rectangles themselves (e.g., such as size, aspect ratio, color, etc.), variations in local combinations of rectangles (e.g., such as at corners), variations in lines, and variations in scale (e.g., markers at multiple scales or markers within markers).

FIGS. 29A, 29B, 29C, 29D, 29E, 29F, 29G, and 29H illustrate some exemplar approaches that can be used to incorporate positional and/or identification information within a discernible marker. FIG. 29A illustrates variations in local combinations of rectangles that can be used at text corner locations. Three exemplary corner types are shown, specifically corner type 1 360, corner type 2 362, and corner type 3 364. Although three are shown, additional corner types can be formulated using four adjacent grid squares. Additionally, other combinations of grid squares can be used to formulate patterns that can be imaged and processed so as to be identified (e.g., a 3 by 3 pattern, a 3 by 2 pattern, etc.). FIGS. 29B and 29C illustrate discernible text constructed using rectangular features selected from a 2-D array (i.e., checkerboard array) of rectangular primitives. FIG. 29D illustrates how a discernible text marker can be configured to have more corner features while still being readable. FIGS. 29E and 29F illustrate how a variation in the amount of overlap between adjacent rectangles can be used to change the appearance of the resulting text (FIG. 29E having no overlap and FIG. 29F having slight overlap, which makes the "cross" point/saddle point look like a cross point). Such an overlap may help compensate where an imaging system dilates the white area(s). FIGS. 29G and 29H illustrates discernible text markers having features at multiple scales. Unlike the marker shown in FIG. 29G, the marker shown in FIG. 29H does not include a second level that is readily discernible by a human viewer, which may be advantageous in certain situations.

FIGS. 30A, 30B, 30C, and 30D illustrate some additional exemplary discernible marker designs. Marker 370 is similar to marker 190 (shown in FIG. 13C), but information dots 194 are replaced with discernible letters 372. Marker 380 is similar to marker 370, but has been extended to multiple rows. Marker 390 is an example where the text background 392 differs from its surroundings 394 so that the rectangular structure of the text background can be used to provide alignment. Marker 400 is similar to marker 390, but includes four corners 402 having saddle points, which are more distinctive relative to surroundings. Marker 410 illustrates the use of a portion of text as a localizer, such as the letter "V" 412 shown, and the rest of the text for identification and/or verification (i.e., error checking/correction). The part (s) chosen for a localizer(s) can be enlarged or modified with more visual features to ensure they can be detected reliably from images. Marker 420 illustrates the use of added localizer features, such as circles 422, that are blended with the text.

Discernible Marker Detection

Figure 31:
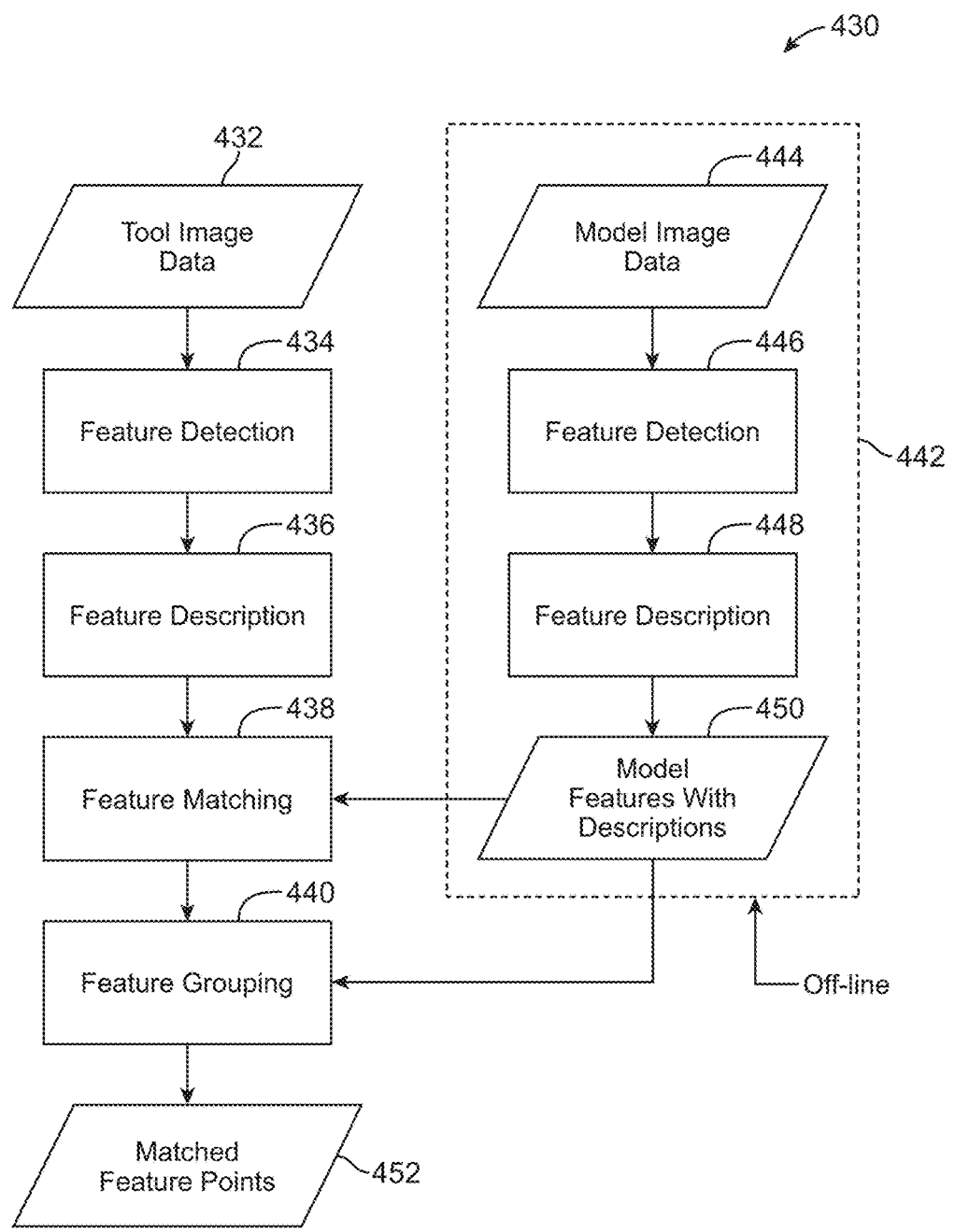
FIG. 31 is a flow diagram of a tool tracking method that employs processing of an image of a surgical tool having a discernible marker, in accordance with embodiments.

FIG. 31 is a flow diagram of a tool tracking method 430 that employs processing of an image of a tool having a discernible marker. The method 430 produces matched feature points that can be used to estimate a 3-D pose for a tool using above described methods.

In step 434 (feature detection), feature points (e.g., corners), which are stable against viewpoint changes, are located (i.e., detected) by processing the tool image data 432. As discussed above, a discernable marker can be configured to boost the number of such stable features, such as by using a rectangular font or by including zigzagged strokes (e.g., see FIG. 29D). A variety of approaches can be used for feature detection. One such approach is to use a corner detector. (See C. Harris and M. Stephens (1988). "A combined corner and edge detector," in *Proceedings of the 4$^{th}$ Alvey Vision Conference:* pages 147-151.) Another approach is to locate distinctive image features from scale-invariant keypoints. (See D. Lowe (2004), "Distinctive Image Features from Scale-invariant Key points," in *International Journal of Computer Vision,* 2004.)

In step 436 (feature description), a description of the neighborhood around a feature point(s) is determined. A variety of approaches can be used for feature description. One such approach is to use adaptive thresholding to convert a gray scale image to a binary image and use Shape Context as the descriptor. (See S. Belongie, J. Malik, and J. Puzicha. "Shape Matching and Object Recognition Using Shape Contexts," in *IEEE Transaction on Pattern Analysis and Machine Intelligence* 2002, which is hereby incorporated by reference.) Another approach is to use Histogram of Orientation as the descriptor on a gray scale image. (see D. Lowe (2004), "Distinctive Image Features from Scale-Invariant Keypoints," in *International Journal of Computer Vision,* 2004, which is hereby incorporated by reference.)

In step 438 (feature matching), individual feature points are matched against feature points from images of models using model features with descriptions data 450. The model feature with descriptions data 450 can be formulated off-line (using 442) by processing model image data 444 so as to detect (step 446) and generate descriptions (step 448) for model features, which can be accomplished using the above described approaches. A number of model images from various viewpoints can be used to facilitate the matching of markers viewed at different viewpoints.

In step 440 (feature grouping), the matched features are grouped so as to enforce geometric constraints among the matched points. Pose estimation and robust estimation can be used during the grouping of the feature points and can provide for outlier rejection of inconsistent feature points. The resulting matched feature points data 452 can be used for tool state estimation using above-described methods.

Integrating Additional Constraint Data

Pose data from multiple time instances can be used in the determination of an object's pose. For example, different video frames over time can provide extra constraint on the pose of an object, such as a minimally invasive surgical instrument, that can be used to help outliers which are not consistent with the constraint.

Kinematic constrains can also be used in the determination of an object's pose. For example, in minimally invasive surgery the surgical instruments are inserted into the patient body through insertion points on the body wall. These insertion points are fixed and surgical tools are constrained to pass through these points. Such insertion point constraint implies that the surgical tool's axes at different times intersect at a common point. Accordingly, a tool pose whose axis does not pass through the insertion point can be classified as an outlier and therefore discarded by using a robust estimation technique, such as RANSAC.

Additionally, as discussed above, kinematics joint data can also be used in the determination of an object's pose. For example, in the context of robotic surgery there is a strong temporal constraint that is provided by using the relationship between an image-derived tool pose and a kinematics-derived tool pose. For details, see commonly owned U.S. Pat. App. Pub. No. 2006/0258938 A1.

Pose data for multiple tools for multiple time instances can be used to identify a tool in an image of two or more tools. For example, when two or more tools in an image have identical markers, an image-derived pose for one of the tools can be compared with an estimated pose for that tool. The estimated pose can be generated by using at least one prior tool state from a prior image of the tool or joint data from a robotic actuation system effectuating movement of the tool. Where the imaged-derived tool pose is within a predetermined deviation of the estimated pose, the identity of the tool can be confirmed.

It is understood that the examples and embodiments described herein are for illustrative purposes and that various modifications or changes in light thereof will be suggested to persons skilled in the art and are to be included within the spirit and purview of this application and the scope of the appended claims. Numerous different combinations are possible, and such combinations are considered to be part of the present invention.

What is claimed is:

1. A tool tracking method for a distal end of a tool, wherein the distal end includes three primitive features having known positions on the tool, wherein each primitive feature includes a spherical reflective surface, wherein the three primitive features include a natural feature of the tool and an artificial feature of the tool, wherein the natural feature includes one of an end of a bolt and an end of a hinge of the tool and is a component of the tool that is provided for either construction or operation of the tool, and wherein the artificial feature is included on the tool to provide the spherical reflective surface, the method comprising:
receiving stereo image data of the three primitive features when the distal end of the tool is within a patient body, wherein the stereo image data captures a bright spot for each of the three primitive features which has been generated by illuminating the primitive feature, the bright spots being substantially aligned with spherical centers of the spherical reflective surfaces of the three primitive features;
generating an estimated tool state for the tool by using at least one prior tool state from the received stereo image data of the tool for a prior time or joint data from a robotic actuation system effecting movement of the tool; and
determining a pose of the tool by processing information of the stereo image data so as to locate the spherical centers by using the bright spots and based on the estimated tool state.

2. A method as in claim 1, wherein a light used for illuminating the three primitive features includes a visible light spectrum.

3. A method as in claim 1, wherein determining the pose of the tool by processing information of the stereo image data is accomplished so as to identify the three primitive features by using specular reflected light.

4. A method as in claim 1, further comprising processing said stereo image data so as to determine three-dimensional positional data for the spherical centers.

5. A method as in claim 4, wherein a constellation algorithm is used to identify a pattern of the primitive features in the stereo image data.

6. A method as in claim 5, further comprising using the estimated tool state in the constellation algorithm.

7. A method as in claim 4, further comprising:
capturing stereo image data for a plurality of time points;
generating an estimated tool state for the plurality of time points; and
rejecting any incompatible pattern detection by using a robust estimation technique.

8. A method as in claim 7, wherein the robust estimation technique used is a Random Sample Consensus (RANSAC) technique.

9. A method as in claim 4, wherein a model based image signature is used in the identification of at least one primitive feature in said stereo image data.

10. A method as in claim 1, further comprising
using the estimated tool state to reject an incompatible pattern detection.

11. A medical system, comprising:
a tool having a distal end that is insertable into a patient body, wherein the distal end has three primitive features having known positions on the tool, wherein each primitive feature comprises a spherical reflective surface, wherein the three primitive features include a natural feature of the tool and an artificial feature of the tool, wherein the natural feature includes one of an end of a bolt and an end of a hinge of the tool and is a component of the tool that is provided for either construction or operation of the tool, and wherein the artificial feature is included on the tool to a spherical reflective surface;
a light source insertable into the patient body so as to be oriented to direct light toward the distal end of the tool when the distal end is within the patient body;
a stereo image capture device insertable into the patient body so that the stereo image capture device captures stereo images of bright spots generated by the light source directing light on the three primitive features, the bright spots substantially aligned with spherical centers of the spherical surfaces; and
a processor coupled to the image capture device and configured to determine a pose of the tool by processing the stereo images so as to locate the spherical centers by using the bright spots and based on an estimated pose of the tool generated by using at least one prior pose of the tool from stereo image data of the tool for a prior time or joint data from a robotic actuation system effecting movement of the tool.

12. A system as in claim 11, further comprising a non-transitory tangible medium comprising machine-readable instructions executable by said processor for processing said stereo images.

13. A system as in claim 11, wherein the bright spots result from specular reflected light.

14. A system as in claim 11, wherein the processor is configured so as to determine three-dimensional positional data for the spherical centers by processing the stereo images.

15. A system as in claim 14, wherein the stereo image capture device comprises a stereoscopic endoscope.

16. A system as in claim 11, wherein the spherical reflective surface comprises a convex or concave surface.

* * * * *